US012138257B2

(12) United States Patent
Li et al.

(10) Patent No.: US 12,138,257 B2
(45) Date of Patent: Nov. 12, 2024

(54) ANTIMICROBIAL COMPOSITIONS

(71) Applicant: Melinta Subsidiary Corp., Morristown, NJ (US)

(72) Inventors: Danping Li, Middlebury, CT (US); Eric S. Burak, East Haddam, CT (US); David S. Dresback, Stonington, CT (US); Danielle B. Lord, Hamden, CT (US)

(73) Assignee: MELINTA SUBSIDIARY CORP., Morristown, NJ (US)

( * ) Notice: Subject to any disclaimer, the term of this patent is extended or adjusted under 35 U.S.C. 154(b) by 901 days.

(21) Appl. No.: 16/425,580

(22) Filed: May 29, 2019

(65) Prior Publication Data

US 2020/0022971 A1     Jan. 23, 2020

Related U.S. Application Data

(63) Continuation of application No. 15/042,886, filed on Feb. 12, 2016, now abandoned, which is a continuation of application No. 13/105,513, filed on May 11, 2011, now abandoned, which is a continuation of application No. PCT/US2009/064220, filed on Nov. 12, 2009.

(60) Provisional application No. 61/199,253, filed on Nov. 15, 2008.

(51) Int. Cl.
| | |
|---|---|
| *A61K 31/4709* | (2006.01) |
| *A61K 9/00* | (2006.01) |
| *A61K 9/08* | (2006.01) |
| *A61K 9/19* | (2006.01) |
| *A61K 31/47* | (2006.01) |
| *A61K 47/18* | (2017.01) |
| *A61K 47/26* | (2006.01) |
| *A61K 47/40* | (2006.01) |
| *A61K 47/69* | (2017.01) |
| *B82Y 5/00* | (2011.01) |

(52) U.S. Cl.
CPC ........ *A61K 31/4709* (2013.01); *A61K 9/0019* (2013.01); *A61K 9/08* (2013.01); *A61K 9/19* (2013.01); *A61K 31/47* (2013.01); *A61K 47/183* (2013.01); *A61K 47/26* (2013.01); *A61K 47/40* (2013.01); *A61K 47/6951* (2017.08); *B82Y 5/00* (2013.01)

(58) Field of Classification Search
CPC .... A61K 31/4709; A61K 47/26; A61K 47/40; A61K 47/183
See application file for complete search history.

(56) References Cited

U.S. PATENT DOCUMENTS

| | | | |
|---|---|---|---|
| 3,426,011 A | 2/1969 | Parmeter et al. | |
| 3,459,731 A | 8/1969 | Gramera et al. | |
| 4,727,064 A | 2/1988 | Pitha | |
| 5,024,998 A | 6/1991 | Bodor | |
| 5,084,276 A | 1/1992 | Yunker et al. | |
| 5,134,127 A | 7/1992 | Stella et al. | |
| 5,376,645 A | 12/1994 | Stella et al. | |
| 5,874,418 A | 2/1999 | Stella et al. | |
| 5,998,436 A | 12/1999 | Yazaki et al. | |
| 6,048,845 A | 4/2000 | Rubinfeld | |
| 6,133,284 A | 10/2000 | Yazaki et al. | |
| 6,156,903 A | 12/2000 | Yazaki et al. | |
| 6,166,012 A | 12/2000 | Muller et al. | |
| 6,407,079 B1 | 6/2002 | Muller et al. | |
| 6,685,958 B2 | 2/2004 | Roy et al. | |
| 8,642,065 B2 | 2/2014 | Hans Moore et al. | |
| 2002/0187193 A1 | 12/2002 | Roy et al. | |
| 2003/0055023 A1* | 3/2003 | Rajewski | B82Y 5/00 514/58 |
| 2005/0065164 A1 | 3/2005 | De Souza et al. | |
| 2006/0228411 A1* | 10/2006 | Wu | A61K 47/32 424/464 |
| 2007/0049552 A1* | 3/2007 | Babu | A61K 47/38 514/58 |
| 2007/0129328 A1 | 6/2007 | Boettner et al. | |
| 2007/0219124 A1 | 9/2007 | Labischinski et al. | |
| 2007/0238720 A1* | 10/2007 | Hopkins | A61K 9/2018 514/210.21 |
| 2009/0036406 A1 | 2/2009 | Nakai et al. | |
| 2010/0048685 A1 | 2/2010 | Ren et al. | |
| 2013/0059826 A1 | 3/2013 | Pipkin et al. | |

FOREIGN PATENT DOCUMENTS

| | | |
|---|---|---|
| CA | 2371942 A1 | 10/2000 |
| CN | 1931369 A | 3/2007 |
| EP | 1764102 A1 | 3/2007 |
| JP | 2006523687 A | 10/2006 |

(Continued)

OTHER PUBLICATIONS

Abilify®, Highlights of Prescribing Information, Otsuka Pharmaceutical Co., Ltd., Tokyo, Japan, 84 pgs. (Jan. 2016).

(Continued)

*Primary Examiner* — Timothy P Thomas
(74) *Attorney, Agent, or Firm* — Wilmer Cutler Pickering Hale and Dorr LLP

(57) ABSTRACT

The present invention relates to antimicrobial compositions and more specifically compositions of quinolone carboxylic acid derivatives. These compositions have improved solubility, stability, and tolerability. These compositions are useful for intravenous administration for treating, preventing, or reducing the risk of infection.

20 Claims, 2 Drawing Sheets

(56) References Cited

FOREIGN PATENT DOCUMENTS

| | | |
|---|---|---|
| JP | 2008515910 A | 5/2008 |
| KR | 1020080075349 A | 8/2008 |
| WO | WO-97/11068 A1 | 3/1997 |
| WO | WO-01/34595 A1 | 5/2001 |
| WO | WO-03039548 A1 | 5/2003 |
| WO | WO-2003050107 | 6/2003 |
| WO | WO-2004089418 A1 | 10/2004 |
| WO | WO-2005/058886 A1 | 6/2005 |
| WO | WO-2005103048 A1 | 11/2005 |
| WO | WO-2006015194 A2 | 2/2006 |
| WO | WO-2006042034 A2 | 4/2006 |
| WO | WO-2006110815 A1 | 10/2006 |
| WO | WO-2006134877 A1 | 12/2006 |
| WO | WO-2007/097888 A2 | 8/2007 |
| WO | WO-2008020904 A2 | 2/2008 |
| WO | WO-2008029282 A2 | 3/2008 |
| WO | WO-2008045673 A2 | 4/2008 |
| WO | WO-2008/085913 A1 | 7/2008 |
| WO | WO-2008091752 A2 | 7/2008 |
| WO | WO-2008126384 A1 | 10/2008 |

OTHER PUBLICATIONS

Ativan™ (lorazepam) Injection, Baxter Healthcare Corporation, Deerfield, IL, USA, 20 pgs. (Nov. 29, 2006).
Beyrich, et al., "Enantioselective Influence of Cyclodextrins on Cleavage of Chiralic Esters," Chirality, vol. 7, pp. 560-564 (1995).
Brewster, M.E. and Loftsson, T., "Cyclodextrins as Pharmaceutical Solubilizers," Advanced Drug Delivery Reviews, vol. 59, pp. 645-666 (2007).
Captisol® Material Safety Data Sheet, MSDS No. CAP-001, Cydex Pharmaceuticals, Inc., Lawrence, KS, USA, 2 pgs. (Feb. 2, 2015).
Cerenia® Data Sheet, Zoetis Inc., Kalamazoo, MI, USA, 2 pgs. (Oct. 2015).
Challa, et al., "Cyclodextrins in Drug Delivery: An Updated Review," AAPS PharmSciTech, vol. 6(2), Article 43, pp. E329-E357 (2005).
Choudhury, S. and Mitra, A.K., "Kinetics of Aspirin Hydrolysis and Stabilization in the Presence of 2-Hydroxypropyl-β-Cyclodextrin," Pharmaceutical Research, vol. 10, No. 1, pp. 156-159 (1993).
Geodon®, Highlights of Prescribing Information, Roerig, Division of Pfizer, Inc., New York, NY, USA, 22 pgs. (Aug. 2015).
Hirayama, et al, "Prominent Inclusion Effect of Dimethyl-β-cyclodextrin on Photoisomerization of the Thromboxane Synthetase Inhibitor (E)-4-(1-Imidazoylmethyl)cinnamic Acid," Journal of Pharmaceutical Sciences, vol. 81, No. 8, pp. 817-822 (Aug. 1992).
Jarho, et al., "Modified β-Cyclodextrin (SBE7-β-CyD) with Viscous Vehicle Improves the Ocular Delivery and Tolerability of Pilocarpine Prodrug in Rabbits," J. Pharm. Pharmacol., vol. 48, pp. 263-269 (1996).
Kyprolis®, Highlights of Prescribing Information, Onyx Pharmaceuticals, Inc., Thousand Oaks, CA, USA, 52 pgs. (Jan. 2016).
Levy, et al., "Side-Effect Evaluation of a New Diazepam Formulation Venous Sequela Reduction Following Intravenous (iv) Injection of a Diazepam Emulsion in Rabbits," Pharmaceutical Research, vol. 6, No. 6, pp. 510-516(1989).
Loftsson, et al., "Cyclodextrins in Drug Delivery," Expert Opin. Drug Deliv., vol. 2, 17 pgs. (2005).
Loftsson, et al., "Self-Association of Cyclodextrins and Cyclodextrin Complexes," J. Pharmaceutical Sciences, vol. 93, No. 5, pp. 1091-1099 (May 2004).
Loftsson, T. and Brewster, M.E., "Pharmaceutical Applications of Cyclodextrins. 1. Drug Solubilization and Stabilization," J. Pharmaceutical Sciences, vol. 85, No. 10, pp. 1017-1025 (Oct. 1996).
Loftsson, T., "Cyclodextrins I: Physicochemical Properties and in vitro Evaluation," AAPS Webinar, University of Iceland, 53 pgs., Mar. 31, 2011.
Loftsson, T., "Cyclodextrins II: Their Pharmakinetics, Safety/Toxicity and in vivo Performance," AAPS Webinar, University of Iceland, 53 pgs., Apr. 7, 2011.
Loftsson, T., "Cyclodextrins," Downloaded from https://notendur.hi.is/thorstlo/general.pdf on Jul. 1, 2016 (36 pgs.).
Loftsson, T., "Effects of Cyclodextrins on the Chemical Stability of Drugs in Aqueous Solutions," Drug Stability, vol. 1, pp. 22-33 (1995).
Lotfsson, T. and Jóhannesson, H.R., "The Influence of Cyclodextrins on the Stability of Cephalotin and Aztreonam in Aqueous Solutions," Pharmazie, vol. 49, pp. 292-293 (1994).
Ma, et al., "Comparative Effects of (SBE)7m-β-CD and HP-β-CD on the Stability of Two Anti-neoplastic Agents, Melphalan and Carmustine," Journal of Pharmaceutical Sciences, vol. 89, No. 2, pp. 275-287 (Feb. 2000).
Ma, et al., "New Injectable Melphalan Formulations Utilizing (SBE)7m-β-CD or HP-β-CD," International Journal of Pharmaceutics, vol. 189, pp. 227-234 (1999).
Del Valle, E.M.M., "Cyclodextrins and Their Uses: A Review," Process Biochemistry, pp. 1-14 (2003).
Narisawa, S. and Stella, V.J., "Increased Shelf-Life of Fosphenytoin: Solubilization of a Degradant, Phenytoin, through Complexation with (SBE)7m-β-CD," J. Pharmaceutical Sciences, vol. 87, No. 8, pp. 926-930 (Aug. 1998).
Nexterone®, Highlights of Prescribing Information, Baxter Healthcare Corporation, Deerfield, IL, USA, 17 pgs. (Mar. 2015).
No Author Listed, "Official Monographs for NF 30," Official Monographs / Betadex, First Supplement to USP 35-NF 30, The United States Pharmacopeial Convention, pp. 5423-5426 (Aug. 1, 2012).
Notice of Preliminary Rejection issued by the Korean Intellectual Property Office for Korean Application No. 1020117013641 dated Jan. 6, 2016 (12 pgs.).
Notice of Reasons for Rejection issued by the Japan Patent Office for Japanese Patent Application No. 2015-002892 mailed Dec. 15, 2015 (11 pgs.).
Noxafil® Label, Merck Sharp & Dohme Corp., 32 pgs. (Nov. 2015).
Rasheed, et al., "Cyclodextrins as Drug Carrier Molecule: A Review," Scientia Pharmaceutica, vol. 76, pp. 567-598 (2008).
Stella, et al., "Mechanisms of Drug Release from Cyclodextrin Complexes," Advanced Drug Delivery Reviews, vol. 36, pp. 3-16 (1999).
Stella, V.J. and He, Q., "Cyclodextrins," Toxicologic Pathology, vol. 36, pp. 30-42 (2008).
Tønnesen, H.H. et al., "Studies of Curcumin and Curcuminoids. XXVII. Cyclodextrin Complexation: Solubility, Chemical and Photochemical Stability," International Journal of Pharmaceutics, vol. 244, pp. 127-135 (2002).
Utsuki, et al., "Different Photodimerization Behaviour of Tranilast in α-, β- and Y-Cyclodextrin Complexes: Cavity-size and Stoichiometry Dependence, "J. Chem. Soc. Perkn. Trans., vol. 2, pp. 109-114 (1993).
Utsuki, et al., "Stoichiometry-dependent Changes of Solubility and Photoreactivity of an Antiulcer Agent, 2'-carboxymethoxy-4,4'-bis(3-methyl-2-butenyloxy)chalcone, in Cyclodextrin Inclusion Complexes," European Journal of Pharmaceutical Sciences, vol. 1, pp. 81-87 (1993).
VFEND®, Highlights of Prescribing Information, Roerig, Division of Pfizer, Inc., New York, NY, USA, 42 pgs. (Feb. 2015).
Wallentine, et al., "Propofol in a Modified Cyclodextrin Formulation: First Human Study of Dose-Response with Emphasis on Injection Pain," Anesthesia & Analgesia, vol. 113, No. 4, pp. 738-741 (Oct. 2011).
Zia, et al., "Effect of Cyclodextrin Charge on Complexation of Neutral and Charged Substrates: Comparison of (SBE)7m-β-CD to HP-β-CD," Pharmaceutical Research, vol. 18, No. 5, pp. 667-673 (2001).
Adachi, et al. "Stabilization of Prostaglandin E1 in Fatty Alcohol Propylene Glycol Ointment by Acidic Cyclodextrin Derivative, O-carboxymethyl-O-ethyl-β-cyclodextrin," Chem. Pharm. Bull., vol. 40, No. 6, pp. 1586-1591 (1992).
Alsarra, et al., "Effect of β-cyclodextrin derivatives on the kinetics of degradation of cefotaxime sodium in solution State," J. Drug Del. Sci. Tech., vol. 17, No. 5, pp. 355-357 (2007).

(56) References Cited

OTHER PUBLICATIONS

Arima, et al., "Comparative Studies of the Enhancing Effects of Cyclodextrins on the Solubility and Oral Bioavailability of Tacrolimus in Rats," Journal of Pharmaceutical Sciences, vol. 90, No. 6, pp. 690-701 (2001).
Banky, et al., "Application of water soluble beta-cyclodextrin in microbiological decomposition of phenol," Journal of the Hungarian Chemical Society, vol. 40, No. 4 pp. 189-192 (1985) (5 total pages).
Bardi, et al., "Hydrocarbon degradation by a soil microbial population with β-cyclodextrin as surfactant to enhance bioavailability," Enzyme and Microbial Technology, vol. 27, pp. 709-713 (2000).
Cutrignelli et al., "Comparative effects of some hydrophilic excipients on the rate of gabapentin and baclofen lactamization in lyophilized formulations," International Journal of Pharmaceutics, vol. 332, pp. 98-106 (2007).
Donova et al., "Modified CDs-Mediated Enhancement of Microbial Sterol Sidechain Degradation," Proceedings of the Eighth International Symposium on Cyclodextrons, pp. 527-530 (1996).
Fava, et al., "Cyclodextrins Enhance the Aerobic Degradation and Dechlorination of Low-Chlorinated Biphenyls," Biotechnology Techniques, vol. 10, No. 4, pp. 291-296 (1996).
Garon, et al., "Effect of Cyclodextrins on Fungal Degradation of Fluorene," Ann. Pharm. FR, vol. 59, pp. 366-368 (2001).
Garon, et al., "Effects of fungal bioaugmentation and cyclodextrin amendment on fluorene degradation in soil slurry," Biodegradation, vol. 15, pp. 1-8 (2004).
Garon, et al., "Enhanced degradation of fluorene in soil slurry by *Absidia cylindrospora* and maltosyl-cyclodextrin," Chemosphere, vol. 56, pp. 159-166 (2004).
Ghorab, et al., "Tablet Formulation Containing Meloxicam and β-Cyclodextrin: Mechanical Characterization and Bioavailability Evaluation," AAPS PharmSciTech., vol. 5, No. 4, pp. 1-6 (2004).
Granados et al., "Effect of Cyclodextrins on the Hydrolysis of Amides," J. Org. Chem., vol. 58, pp. 1771-1777 (1993).
Hara, et al., "Prominent Solubilizing Effect of 2-Hydroxypropyl-β-cyclodextrin on a New Thiazolidine Derivative (FPFS-410) with Antidiabetic and Lipid-lowering Activities through Inclusion Complex Formation," Journal of Inclusion Phenomena and Macrocyclic Chemistry, vol. 56, pp. 135-139 (2006).
Hirayama, et al., "Improvement of chemical instability of prostacyclin in aqueous solution by complexation with methylated cyclodextrins," International Journal of Pharmaceutics, vol. 35, pp. 193-199 (1987).
Hirayama, et al., "Improving the Aqueous Stability of Prostaglandin $E_2$ and Prostaglandin $A_2$ by Inclusion Complexation with Methylated-β-Cyclodextrins," Chem. Pharm. Bull., vol. 32, No. 10, pp. 4237-4240 (1984).
Horikawa, et al., "In vivo and In-vitro Correlation for Delayed-release Behaviour of a Molsidomine/O-carboxymethyl-O-ethyl-β-cyclodextrin Complex in Gastric Acidity-Controlled Dogs," J. Pharm. Pharmacol., vol. 47, pp. 124-127 (1995).
Horiuchi, et al., "Improvement of Stability and Bioavailability of 1-Hexylcarbamoyl-5-fluorouracil (HCFU) by O-carboxymethyl-O-ethyl-β-cyclodextrin," Yakugaku Zasshi, vol. 111, No. 10, pp. 592-599 (1991).
Ikeda, et al., "NMR Spectroscopic Characterization of Metoprolol/Cyclodextrin Complexes in Aqueous Solution: Cavity Size Dependency," Journal of Pharmaceutical Sciences, vol. 93, No. 7, pp. 1659-1671 (2004).
Irie, et al., "Pharmaceutical Applications of Cyclodextrins. III. Toxicological Issues and Safety Evaluation," Journal of Pharmaceutical Sciences, vol. 86, No. 2, pp. 147-162 (1997).
Jeong, et al., "Improvement in some physicochemical and biological properties of LG106W by inclusion complexation with β-cyclodextrin and its derivatives," J. Cosmet. Sci., vol. 51, pp. 227-237 (2000).
Kalac, et al., "Synthetic Models of Enzymes, "Chemické Listy, vol. 66, pp. 1299-1304 (1972).
Kasatani, et al., "A Physico-Chemical Aspect of Cyanine Dye-Cyclomaltooligosaccharide Systems: Enchanced Dimerization of the Dye and Shortening of the Lifetime of the Photoisomer," Carbohydrate Research., vol. 192, pp. 197-214 (1989).
Kikuchi, et al., "Improvement of Chemical Instability of Carmoful in β-Cyclodextrin Solid Complex by Utilizing Some Organic Acids," Chem. Pharm. Bull., vol. 35, No. 1, pp. 315-319 (1987).
Kong, et al., "Influence of cyclodextrin on the biodegradation of nitrobenzene," China Environmental Science, vol. 24, No. 5, pp. 576-578 (2004).
Loftsson, et al., "Cyclodextrin-accelerated degradation of β-lactam antibiotics in aqueous solutions," International Journal of Pharmaceutics, vol. 67, pp. R5-R7 (1991).
Masson, et al., "Stabilisation of ionic drugs through complexation with non-ionic and ionic cyclodextrins," International Journal of Pharmaceutics, vol. 164, pp. 45-55 (1998).
Miyake, et al., "Enhanced Absorption of Cyclosporin A by Complexation with Dimethyl-β-Cyclodextrin in Bile Duct-Cannulated and -Noncannulated Rats," Biol. Pharm. Bull., vol. 22, No. 1, pp. 66-72 (1999).
Okimoto, et al., "The Interaction of Charged and Uncharged Drugs with Neutral (HP-β-CD) and Anionically Charged (SBE7-β-CD) β-Cyclodextrins," Pharmaceutical Research, vol. 13, No. 2, pp. 256-264 (1996).
Ou, et al., "*Chryseobacterium* Sp. Degrade Methyl tert-butyl ether (MTBE) Immobilized by β-cyclodextrin," Journal of Agro-Environment Science, vol. 26, No. 4, pp. 1459-1463 (2007).
Ploemen, et al., "Intravenous tolerability of an acid vehicle in Sprague Dawley rats and beagle dogs after daily slow bolus injection and infusion for one hour during 14 days," Laboratory Animals, vol. 36, pp. 181-187 (2002).
Reid, et al., "Influence of Hydroxypropyl-β-Cyclodextrin on the Extraction and Biodegradation of Phenanthrene in Soil," Environmental Toxicology and Chemistry, vol. 23, No. 3, pp. 550-556 (2004).
Sato, et al., "Improvement of Local Irritation induced with Intramuscular Injection of Tiamulin by Cyclodextrin Complexation," Yakugaku Zasshi, vol. 102, No. 9, pp. 874-880 (1982).
Schwartz, et al., "Cyclodextrin-Enhanced Degradation of Toluene and p-Toluic Acid by *Pseudomonas putida*," Applied and Environmental Microbiology, vol. 61, No. 7, pp. 2727-2731 (1995).
Shiotani, et al., "Characterization of the Inclusion Mode of β-Cyclodextrin Sulfate and its Effect on the Chlorpromazine-Induced Hemolysis of Rabbit Erythrocytes," Chem. Pharm. Bull., vol. 42, No. 11, pp. 2332-2337 (1994).
Uekama, et al., "Enhanced Bioavailability of Digoxin by γ-Cyclodextrin Complexation," J. Pharm. Dyn., vol. 4, pp. 735-737 (1981).
Uekama, et al., "Cyclodextrin Drug Carrier Systems," Chem. Rev., vol. 98, pp. 2045-2076 (1998).
Uekama, et al., "Improvements of Dissolution Characteristics and Chemical Stability of 16,16-Dimethyl-trans-Δ2-prostaglandin $E_1$ Methyl Ester by Cyclodextrin Complexation" Journal of Pharmaceutical Sciences, vol. 68, No. 8, pp. 1059-1060 (1979).
Uekama, et al., "New Perspectives in Cyclodextrin Pharmaceutical Applications: Cyclodextrin Derivatives as New Drug Carriers," Drug Investigation, vol. 2, Suppl. 4, pp. 22-28 (1990).
Uekama, et al., "Stabilizing and Solubilizing Effects of Sulfobutyl Ether β-Cyclodextrin on Prostaglandin $E_1$ Analogue," Pharmaceutical Research, vol. 18, No. 11, pp. 1578-1585 (2001).
Uekama, K., "Design and Evaluation of Cyclodextrin-Based Drug Formulation," Chem. Pharm. Bull., vol. 52, No. 8, pp. 900-915 (2004).
Uekama, K., "Pharmaceutical Application of Cyclodextrins as Multi-Functional Drug Carriers," Yakugaku Zasshhi—Journal of the Pharmaceutical Society of Japan, vol. 124, No. 12, pp. 909-935 (2004).
Wang, et al., "Biodegradation Influence of Cyclodextrin on Mixed System of Nitrobenzene and P-Nitrophenol," China Environmental Science, vol. 24, No. 4, pp. 429-432 (2004).
Wang, et al., "Venous Irritation, Pharmacokinetics, and Tissue Distribution of Tirilazad in Rats Following Intravenous Administration of a Novel Supersaturated Submicron Lipid Emulsion," Pharmaceutical Research, vol. 16, No. 6, pp. 930-938 (1999).
Yalkowsky, et al., "Formulation-Related Problems Associated with Intravenous Drug Delivery," Journal of Pharmaceutical Sciences, vol. 87, No. 7, pp. 787-796 (1998).

(56) References Cited

OTHER PUBLICATIONS

Yamamoto et al., "Improvement of Stability and Dissolution of Prostaglandin $E_1$ by Maltosyl-β-cyclodextrin in Lyophilized Formulation," Chem. Pharm. Bull., vol. 40, No. 3, pp. 747-751 (1992).
Yoshida, et al., "Improvement of Chemical Instability of Digitoxin in Aqueous Solution by Complexation with β-Cyclodextrin Derivatives," Chem. Pharm. Bull., vol. 36, No. 10, pp. 4075-4080 (1988).
Yoshida, et al., "Pharmaceutical Evaluation of Hydroxyalkylated β-Cyclodextrin Derivatives," J. Pharmacobio-Dyn, vol. 12 (1989) (1 page total).
Zhang, et al., "Inclusion Effect of Alpha-Cyclodextrin on Chemical Degradaton of Malathionin Water," Arch. Environ. Contam. Toxicol., vol. 54, pp. 355-362 (2008).
Zhou, et al., "Effect of Tween 80 and β-cyclodextrin on degradation of decabromodiphenyl ether (BDE-209) by White Rot Fungi," Chemosphere, vol. 70, pp. 172-177 (2007).
Basavaraj, et al., "Bioavailability Enhancement of Poorly Water Soluble and Weakly Acidic New Chemical Entity with 2-Hydroxyproply-beta-cyclodextrin Selection of Meglumine, a Polyhydroxy Base, as a Novel Ternary Component," Pharmaceutical Development and Technology, vol. 11, No. 4, pp. 443-451 (2006).
Harnett, et al., "Comparative Study of the in vitro Activity of a New Fluoroquinolone, ABT-492," Journal of Antimicrobial Chemotherapy, vol. 53, pp. 783-792 (Mar. 31, 2004).
Rajewski, et al., "Preliminary Safety Evaluation of Parenterally Administered Sulfoalkyl Ether β-Cyclodextrin Derivatives," J. Pharm. Sciences, vol. 84(8), pp. 927-932 (1995).
International Search Report and Written Opinion for International Application No. PCT/US2009/064220 mailed Jun. 1, 2010 (10 pages).
Search Report and Written Opinion for Singapore Patent Application No. 201103403-0 mailed Sep. 21, 2012 (16 pages).
Supplementary European Search Report for Application No. EP09826758 dated Oct. 7, 2014 (7 pages).
Ribiero, et al., "Investigation and Physicochemical Characterization of Vinpocetine-Sulfobutyl Ether β-Cyclodextrin Binary and Ternary Complexes," Chem. Pharm. Bull., vol. 51(8), pp. 914-922 (2003).
CNCCC Sichuan Co., Ltd, "Meglumine," Downloaded from http://www.cnccc-sc.com/productsshow.aspx?productsIDS=8&cateld=47 on Jan. 29, 2015 (1 pg.).
Thompson, D.O., "Cyclodextrins—Enabling Excipients: Their Present and Future Use in Pharmaceuticals," Critical Reviews™ in Therapeutic Drug Carrier Systems, vol. 14(1), pp. 1-104 (1997).
C. Suryanarayana et al., "Practical Aspects of X-Ray Diffraction", Springer Science and Business Media, Chapter 3, pp. 63-94 (1998).
J. Bauer, "Polymorphism—A Critical Consideration in Pharmaceutical Development, Manufacturing, and Stability", Journal of Validation Technology, 15, pp. 15-23 (2008) available at http://www.ivtnetwork.com/sites/default/files/Polymorphism_01.pdf.
J. Szejtli, "Cyclodextrins in Drug Formulations: Part II", Pharmaceutical Technology, vol. 15, No. 8, pp. 24-38 (Aug. 1991).
Declaration Under 37 C.F.R. § 1.132 of Dr. Valentino J. Stella for U.S. Appl. No. 13/586,380, consisting of 12 pages (filed on Nov. 3, 2016 with United States Patent and Trademark Office).
Mitozytrex™ (mitomycin for injection) Label, consisting of 14 pages (dated Nov. 2002).
Vfend® I.V. (voriconazole) for Injection; Injection; Vfend® Tablets (voriconazole) and Vfend® (voriconazole) for Oral Suspension Label, consisting of 50 pages (dated Mar. 2008).
"Food and Drug Administration Jun. 9, 1999 Trovan (Trovafloxaci1611latrofloxacin Mesylate", http://www.fda.gov/ForConsumers/ConsumerUpdates/ucm053103.htm, consisting of 3 pages, (last updated Dec. 7, 2014).
Rajewski, et al., "Pharmaceutical Applications of Cyclodexxtrins. 2. In Vivo Drug Delivery", Journal of Pharmaceutical Sciences, vol. 85, No. 1, pp. 1143-1169 (Nov. 1996).
Uekama, et al., "Application of Cyclodextrins", Drug Absorption Enhancement—Concepts, Possibilities, Limitations and Trends, pp. 411-456 (1994).
J. Szejtli, "Cyclodextrins and Their Inclusion Complexes", Akadémiai Kiadó, Budapest, pp. 21, 75-86, and 99-101 (25 pages total) (1982).
Mosher, et al., "Sulfobutylether β-Cyclodextrin", Handbook of Pharmaceutical Excipients, Fifth Edition, pp. 754-757, (2006).
"Fruilimicin B Analogues for Gram-positive Bacteria", https://www.uniquest.com.au/filething/get/12065/Fruilimicin-B%20Analogues%20for%20Gram-positive%20Bacteria%20UniQuest, Uniquest, consisting of 2 pages (2015).
Sporanox® (Itraconazole) Oral Solution label, NDA20-657/S-010, Janssen Pharmaceutica N.V., pp. 3-30 (Sep. 2003).
Hernàndez-Borrell, J. and Montero, M.T., "Calculating Microspecies Concentration of Zwitterion Amphoteric Compounds: Ciprofloxacin as Example," Journal of Chemical Education, vol. 74, No. 11, pp. 1311-1314 (Nov. 1997).
"Official Monographs for NF 30," First Supplement to USP 35-NF 30, Official Monographs/Betadex, pp. 5423-5426, The United States Pharmacopeial Convention (Aug. 1, 2012).
Zhanel, G.G., et al., "The new fluoroquinolones: A critical review," Can. J. Infect. Dis., vol. 10. No. 3, pp. 207-238 (May/Jun. 1999).
Ba, et al., "Activity of Gatifloxacin in an In Vitro Pharmacokinetic-Pharmacodynamic Model against *Staphylococcus aureus* Strains either Susceptible to Ciprofloxacin or Exhibiting Various Levels and Mechanisms of Ciprofloxacin Resistance," Antimicrobial Agents and Chemotherapy, vol. 50, No. 6, pp. 1931-1936 (Jun. 2006).
Brighty, K.E. and Gootz, T.D., "The chemistry and biological profile of trovafloxacin," Journal of Antimicrobial Chemotherapy, vol. 39, Suppl. B, pp. 1-14 (1997).
Cavet, M.E., et al., "Fluoroquinolone (ciprofloxacin) secretion by human intestinal epithelial (Caco-2) cells," British Journal of Pharmacology, vol. 121, pp. 1567-1578 (1997).
Davis, M.E. and Brewster, M.E., "Cyclodextrin-based pharmaceutics: past, present and future," Nat. Rev. Drug. Discov., vol. 3, pp. 1023-1035 (Dec. 2004).
Langlois, M.-H., et al., "Protonation equilibrium and lipophilicity of moxifloxacin," Journal of Pharmaceutical and Biomedical Analysis, vol. 37, pp. 389-393 (2005).
Lemaire, S., et al., "Contrasting Effects of Acidic pH on the Extracellular and Intracellular Activities of the Anti-Gram-Positive Fluoroquinolones Moxifloxacin and Delafloxacin against *Staphylococcus aureus*," Antimicrobial Agents and Chemotherapy, vol. 55, No. 2, pp. 649-658 (Feb. 2011).
Loftsson, T. and Duchene, D., "Cyclodextrins and their pharmaceutical applications," Int. J. Pharm., vol. 329, pp. 1-11 (2007).
Naber, C.K., et al., "Concentrations of Gatifloxacin in Plasma and Urine and Penetration into Prostatic and Seminal Fluid, Ejaculate, and Sperm Cells after Single Oral Administrations of 400 Milligrams to Volunteers," Antimicrobial Agents and Chemotherapy, vol. 45, No. 1, pp. 293-297 (Jan. 2001).
Okeri, H.A. and Arhewoh, I.M., "Analytical profile of the fluoroquinolone antibacterials. I. Ofloxacin," African Journal of Biotechnology, vol. 7, No. 6, pp. 670-680 (Mar. 18, 2008).
Stella, V.J. and Rajewski, R.A., "Cyclodextrines: their future in drug formulation and delivery," Pharm. Res., vol. 14, No. 5, pp. 556-567 (1997).
Varanda, F., et al., "Solubility of Antibiotics in Different Solvents. 1. Hydrochloride Forms of Tetracycline, Moxifloxacin, and Ciprofloxacin," Ind. Eng. Chem. Res., vol. 45, pp. 6368-6374 (2006).
Völgyi, G., et al., "Predicting the exposure and antibacterial activity of fluoroquinolones based on physicochemical properties," European Journal of Pharmaceutical Sciences, vol. 47, pp. 21-27—8 pages in total (2012).
Bodor, N., et al., "Effect of cyclodextrins on the solubility and stability of a novel soft corticosteroid, loteprednol etabonate," Pharmazie, vol. 55, No. 3, pp. 206-209 (2000).
Dyloject™ (diclofenac sodium), Injection, Hospira, Inc., Lake Forest, Illinois USA, 17 total pages (Revised Dec. 2014).
Irie, T. and Uekama, K., "Pharmaceutical Applications of Cyclodextrins. III. Toxicological Issues and Safety Evaluation," Journal of Pharmaceutical Sciences, vol. 86, No. 2, pp. 147-162 (Feb. 1997).
Irie, T., et al.., "Cyclodextrin-Induced Hemolysis and Shape Changes of Human Erythrocytes in Vitro," J. Pharm. Dyn., vol. 5, pp. 741-744 (1982).

(56) References Cited

OTHER PUBLICATIONS

Jarho, P., et al., "Cyclodextrin-Catalyzed Deacetylation of Spironolactone is pH and Cyclodextrin Dependent," Journal of Pharmaceutical Sciences, vol. 89, No. 2, pp. 241-249 (Feb. 2000).
Jóhannsdóttir, S., et al., "Development of a cyclodextrin-based aqueous cyclosporin A eye drop formulations," International Journal of Pharmaceutics, vol. 493, pp. 86-95 (Jul. 26, 2015).
Loftsson, T. and Masson, M., "Complexation Properties of $_\beta$-cyclodextrin Sulfobutylether Sodium Salt," Proceedings of the Ninth International Symposium on Cyclodextrins, Santiago de Compostela, Spain, May 31-Jun. 3, 1998, Edited by J.J.T. Labandeira and J.L. Vila-Jato (5 total pages).
Loftsson, T. and Petersen, D.S., "Cyclodextrin Solubilization of ETH-615, a Zwitterionic Drug," Drug Development and Industrial Pharmacy, vol. 24, No. 4, pp. 365-370 (1998).
Loftsson, T. and Petersen, D.S., "Cyclodextrin solubilization of water-insoluble drugs: calcipotriol and EB-1089," Pharmazie, vol. 52, No. 10, pp. 783-785 (1997).
Loftsson, T. and Stefansson, E., "Cyclodextrins in eye drop formulations: enhanced topical delivery of corticosteroids to the eye," Acta Ophthalmologica Scandinavica, vol. 80, pp. 144-150 (2002).
Loftsson, T., et al., "Cyclodextrin solubilization of benzodiazepines: formulation of midazolam nasal spray," International Journal of Pharmaceutics, vol. 212, pp. 29-40 (2001).
Loftsson, TH. and Jóhannesson, H.R., "The influence of cyclodextrins on the stability of cephalotin and aztreonam in aqueous solutions," Pharmazie, vol. 49, vol. H.4, pp. 292-293 (1994).
Lotemax™—Sterile Ophthalmic Suspension (loteprednol etabonate—ophthalmic suspension, 0.5%), Bausch & Lomb Pharmaceuticals, Inc., Tampa Florida USA, 16 total pages (Mar. 6, 1998).
Popielec, A., et al., "Effect of cyclodextrins on the degradation rate of benzylpenicillin," Pharmazie, vol. 71, pp. 68-75 (2016).
Saokham, P. and Loftsson, T., "Y-Cyclodextrin," International Journal of Pharmaceutics, vol. 516, pp. 278-292 (2017).
Stella, V.J., "Fundamentals of Drug Stability and Compatibility," Handbook of Injectable Drugs, L. Trissel, ed., American Society of Hospital Pharmacists, Introduction—pp. XI-XXII (1986).
Van Bambeke, F., "Delafloxacin, a non-zwitterionic fluoroquinolone in Phase III of clinical development: evaluation of its pharmacology, pharmacokinetics, pharmacodynamics and clinical efficacy," Future Microbiology, vol. 10, No. 7, pp. 1111-1123 (2015).
Wang, J. and Song, A., "Progress in Pharmaceutical Applications of a New Excipient Sulfobutyl-β- Cyclodextrins," Material Guide, vol. 21, Issue 3, pp. 40-43 (Mar. 2007) with English translation (8 total pages).
"Encyclopedia of Pharmaceutical Excipients," chief editors: Mingsheng Luo and Tianhui Gao, Sichuan Publishing Group, Sichuan Science and Technology press, second edition in Chengdu in Jan. 2006, cover page, publication page, catalogue page, pp. 1301-1303 with English translation of cover pages and pp. 1302-1303 (44 total pages).
No Author Listed, "Pharmaceutical Excipient Ethylene Diamine Tetraacetic Acid Disodium," Medical Industry Standard of the People's Republic of China YY206-95, pp. 7-10, published on Aug. 1, 1995 with English translation of p. 7 (5 total pages).
No Author or Editor Listed, "Chapter 2: Preparation of Technology of Inclusion Compound," of "New Techniques and New Dosage Forms of Drugs," People's Medical press with cover page, copyright page, catalogue page, and pp. 33-34, 2nd edition (May 2005) with English translation of cover page and pp. 33-34 (44 total pages).
"Design and Application of Freeze-dried Drug Preparation Technology," compiled by Yao Jing and Zhang Ziqiang, China Medical Press, the first printing of the first edition in May 2007, cover page, copyright page, catalogue page, and pp. 141-148 with English translation of cover page, abstract, pp. 141-148 (34 total pages).
"Pharmaceutical Preparation Technology," chief editors: Ling Peixue and Zhang Tianmin, Eleventh Five-Year Plan National Planning Textbook for General Higher Education—China Light Industry press, the first printing of the first edition in Jun. 2007, cover page, copyright page, catalogue page, pp. 124-128 with English translation of cover pages and pp. 124-128 (30 total pages).
"Chapter 2: Excipients for Liquid Preparations," Pharmaceutical Excipients, chief editor: Chaomei Fu and Shiya Wang, New Century National Traditional Chinese Medical University Innovative Textbook—Traditional Chinese Medicine Press, the first edition in Oct. 2008, cover page, copyright page, catalogue page, pp. 112-116 with English translation of cover page and pp. 113-114 (22 total pages).
"Pharmacy of Traditional Chinese Medicine (For Traditional Chinese Medicine Pharmacology Professional)," chief editor: Ming Yang, Traditional Chinese Medicine Textbook for National General Higher Education - Shanghai Science and Technology press, Aug. 2008, cover page, copyright page, catalogue page, pp. 296-300 with English translation of cover page and p. 298 (32 total pages).
"Pharmacy," chief editor: Ning Lin, Planning Textbook of Pharmacy and Bioengineering for Institution of Higher Education—Hubei Changjiang Press, Hubei Science and Technology Press, the first printing of the first edition in Dec. 2007, cover page, copyright page, catalogue page, pp. 47-51 with English translation of cover page and p. 49 (26 total pages).
Notification of Request for Invalidation by Jiangsu Aosaikang Pharmaceutical Incorporated Company against Chinese Patent No. ZL200980145980.1 issued Chinese Patent Office on Mar. 16, 2021 with English translation (40 total pages).
Notification of Request for Invalidation by Jiangsu Aosaikang Pharmaceutical Incorporated Company against Chinese Patent No. ZL201410002645.9 issued Chinese Patent Office on Mar. 16, 2021 with English translation (50 total pages).
Notification of Request for Invalidation by Jiangsu Aosaikang Pharmaceutical Incorporated Company against Chinese Patent No. ZL201510257577.5 issued Chinese Patent Office on Mar. 16, 2021 with English translation (44 total pages).
Examination Decision on Invalidation issued on Sep. 30, 2021 by China National Intellectual Property Administration in Chinese Patent No. 200980145980.1 with English translation (29 total pages).
Examination Decision on Invalidation issued on Sep. 30, 2021 by China National Intellectual Property Administration in Chinese Patent No. 201410002645.9 with English translation (40 total pages).
Examination Decision on Invalidation issued on Sep. 30, 2021 by China National Intellectual Property Administration in Chinese Patent No. 201510257577.5 with English translation (32 total pages).
Examination Report issued by Intellectual Property Registry of Guatemala on Oct. 5, 2022 in Guatemalan Patent Application No. A-2011-00119 with English translation (8 total pages).
Examination Report issued by Intellectual Property Corporation of Malaysia on Jul. 29, 2022 in Malaysian Patent Application No. PI2020004141 (2 total pages).
Office Action issued May 16, 2023 by Guatemalan Patent Office in Guatemalan Patent Application No. A 2011-00119 with English translation (9 total pages).
Hearing Notice issued Jan. 12, 2023 by Indian Patent Office in Indian Patent Application No. 2465/KOLNP/2011 (2 total pages).
Controller's Decision issued Mar. 20, 2023 by Indian Patent Office in Indian Patent Application No. 2465/KOLNP/2011 (17 total pages).
Communication pursuant to Article 94(3) EPC issued on Mar. 3, 2022 by European Patent Office in European Patent Application No. 09826758.6 (4 total pages).
Office Action issued on Mar. 4, 2022 by Guatemalan Patent Office in Guatemalan Patent Application No. A2011-00119 with English translation (6 pages).
Technical Report issued on Apr. 21, 2022 by El Salvadorian Patent Office in El Salvadorian Patent Application No. 3907.2011 with English translation (4 pages).

\* cited by examiner

ANTIMICROBIAL COMPOSITIONS

REFERENCE TO RELATED APPLICATIONS

This application is a continuation of U.S. patent application Ser. No. 13/105,513, filed May 11, 2011, which claims the benefit of International Application No. PCT/US2009/064220, filed Nov. 12, 2009, which claims the benefit U.S. Provisional Application No. 61/199,253, filed Nov. 15, 2008, the entire disclosures of which are incorporated herein by reference.

FIELD OF THE INVENTION

The present invention relates to pharmaceutical compositions comprising a quinolone carboxylic acid derivative antimicrobial compound and a cyclodextrin. These compositions have improved solubility, stability, and tolerability. These compositions are useful for intravenous administration for treating, preventing, or reducing the risk of infection.

BACKGROUND

An appropriate pharmaceutical carrier system is generally a requirement for the safe and effective delivery of a pharmaceutical drug active. The entire pharmaceutical composition, i.e., the pharmaceutical drug active formulated in a pharmaceutical carrier, can affect the bioavailability and also the pharmacokinetics and pharmacodynamics of the drug active. It is therefore important that a pharmaceutical composition be carefully developed and manufactured to deliver the desired pharmaceutical drug active in a safe and effective manner.

The delivery of antimicrobial agents for treating or preventing microbial infections can present special challenges. To provide therapeutic efficacy, it is generally desired that the antimicrobial agent be administered to the patient to achieve systemic concentrations in the bloodstream or target organs above a minimum inhibitory concentration (MIC) for a sufficient time against the particular microbial organism or organisms being targeted. Consequently, an antimicrobial agent that otherwise exhibits an effective antimicrobial profile in vitro can be ineffective, or even harmful, unless properly formulated for in vivo administration.

The challenge of developing suitable antimicrobial compositions is further complicated for the development of liquid formulations for parenteral administration, such as intravenous administration. Intravenous delivery of a drug active is an important route of administration where the drug cannot be administered orally or by other means, for example where a patient is unconscious, or seriously ill, and cannot otherwise take the drug orally. Although not the case with the pyridine carboxylic acid antimicrobial agents of the present invention, many drugs cannot be delivererd orally because of low oral bioavailability or low oral toleration. The development of suitable compositions for intravenous administration often pose many and often complex challenges including balancing the interplay of, solubility of the drug active, chemical and physical stability of the composition, and toleration of the composition upon infusion. In addition to solubility, stability, and toleration, other considerations include ease of manufacture of the composition, convenience of storing the composition, and ease of reconstitution of the composition, e.g., in the case of compositions which are in the form of dry powders or lyophils designed for reconstitution prior to administration.

Solubility of the pharmaceutical drug active is an important consideration, if not the primary consideration, for a product intended for intravenous administration because without sufficient solubility, the pharmaceutical drug active might not be suitable for intravenous administration. Also, limitations on the volume of an intravenous formulation that can be safely and conveniently administered will further constrain the parameters for developing a practical formulation. If the pharmaceutical drug active cannot be solubilized at a practical level, then it might not even be possible to develop an intravenous formulation of the drug.

Stability of a pharmaceutical composition is another important consideration. A pharmaceutical composition must have sufficient chemical and physical stability such that the potency of the pharmaceutical drug active is maintained above a required level and the integrity of the overall formulation is maintained to enable safe administration. It is important that the formation of potentially harmful degredants and byproducts is minimized.

Tolerability of a pharmaceutical composition is yet another important consideration, because an intravenous formulation should not irritate or damage the blood vessels and surrounding tissue of the patient. Furthermore, the composition should not cause undue venous intoleration or undue discomfort during administration, or alternatively should reduce venous intoleration or discomfort.

A pharmaceutical composition should have sufficient efficacy. A pharmaceutical composition should also have sufficient chemical and physical stability to enable administration to a patient. A pharmaceutical composition should also maintain the potency of the drug active over a useful length of time. Potency of a drug active in a pharmaceutical composition can be maintained, for example, by keeping the concentration or level of the drug active constant, or nearly constant, in the composition over time.

Therefore, the present invention addresses the foregoing and other needs.

SUMMARY OF THE INVENTION

Figure 1:
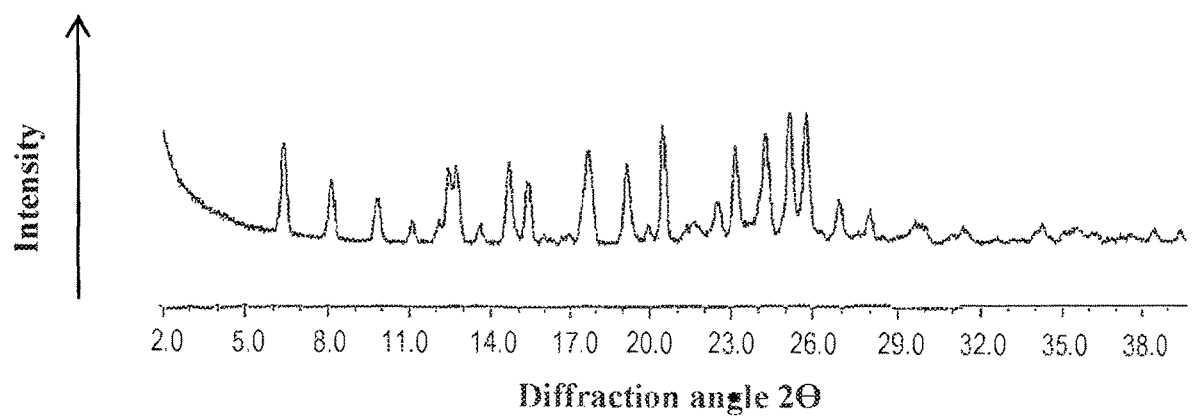
FIG. 1 shows a powder X-ray diffraction pattern of crystalline D-glucitol, 1-deoxy-1-(methylamino)-, 1-(6-amino-3,5-difluoropyridin-2-yl)-8-chloro-6-fluoro-1,4-dihydro-7-(3-h-ydroxyazetidin-1-yl)-4-oxo-3-quinolinecarboxylate (salt).

The present invention relates to antimicrobial compositions and more specifically compositions of quinolone carboxylic acid derivatives. The present invention relates to a pharmaceutical composition comprising a quinolone carboxylic acid derivative or a pharmaceutically acceptable salt or ester thereof, and a cyclodextrin selected from the group consisting of an alpha-cyclodextrin, a beta-cyclodextrin, a gamma-cyclodextrin, and mixtures thereof. These compositions have improved solubility of the drug active, improved chemical and physical stability, i.e. improved stability of the drug active and of the overall composition, and improved tolerability for intravenous administration or injection.

These compositions are useful for intravenous administration or injection, for treating, preventing, or reducing the risk of infection.

In one aspect, the invention relates to a pharmaceutical composition which prior to mixing comprises (a) a quinolone carboxylic acid derivative or a pharmaceutically acceptable salt or ester thereof, and (b) a cyclodextrin.

In one aspect, the invention relates to a pharmaceutical composition which prior to mixing comprises (a) a quinolone carboxylic acid derivative or a pharmaceutically acceptable salt or ester thereof, (b) a cyclodextrin, and (c) a chelating agent.

In one aspect, the invention relates to a pharmaceutical composition comprising (a) a quinolone carboxylic acid derivative or a pharmaceutically acceptable salt or ester thereof, an (b) a cyclodextrin.

In one aspect, the invention relates to a pharmaceutical composition comprising (a) a quinolone carboxylic acid derivative or a pharmaceutically acceptable salt or ester thereof, (b) a cyclodextrin, and (c) a chelating agent.

In one aspect, the invention relates to a pharmaceutical composition comprising an inclusion complex, said inclusion complex comprising (a) a quinolone carboxylic acid derivative or a pharmaceutically acceptable salt or ester thereof, and (b) a cyclodextrin.

In one aspect, the invention relates to a pharmaceutical composition comprising (a) an inclusion complex, said inclusion complex further comprising (i) a quinolone carboxylic acid derivative or a pharmaceutically acceptable salt or ester thereof, and (ii) a cyclodextrin; and (b) a chelating agent.

In one aspect, the invention relates to a pharmaceutical composition comprising (that is in the form of) an aqueous solution.

In one aspect, the invention relates to a pharmaceutical composition comprising (that is in the form of) a dry mixture. In one aspect, the invention relates to a pharmaceutical composition wherein said dry mixture is a lyophile. In one aspect, the invention relates to a pharmaceutical composition wherein said dry mixture is made by lyophylization. In one aspect, the invention relates to a pharmaceutical composition wherein said dry mixture or lyophile is reconstituted. In one aspect, the invention relates to a pharmaceutical composition wherein said pharmaceutical composition is diluted.

In one aspect, the invention relates to a pharmaceutical composition wherein said cyclodextrin is selected from the group consisting of alpha-cyclodextrins, beta-cyclodextrins, gamma-cyclodextrins, and mixtures thereof. In one aspect, the invention relates to a pharmaceutical composition said cyclodextrin is selected from the group consisting of beta-cyclodextrins, gamma-cyclodextrins, and mixtures thereof. In one aspect, the invention relates to a pharmaceutical composition wherein said cyclodextrin is a beta-cyclodextrin.

In one aspect, the invention relates to a pharmaceutical composition wherein said cyclodextrin is a beta-cyclodextrin selected from the group consisting of a beta-cyclodextrin ether, a beta-cyclodextrin ester, and mixtures thereof. In one aspect, the invention relates to a pharmaceutical composition wherein said cyclodextrin is a hydroxyalkyl-beta-cyclodextrin. In one aspect, the invention relates to a pharmaceutical composition wherein said hydroxyalkyl-beta-cyclodextrin is a hydroxypropyl-beta-cyclodextrin.

In one aspect, the invention relates to a pharmaceutical composition wherein said cyclodextrin is a beta-cyclodextrin corresponding to the following formula (3) (beta-cyclodextrin)-OR (3) in which the residues R are hydrogen or hydroxyalkyl groups and part of the residues R may optionally be alkyl groups, the beta-cyclodextrin ether having a water-solubility of more than 1.8 g in 100 ml water. In one aspect, the invention relates to a pharmaceutical composition wherein R is selected from the group consisting of hydroxyethyl, hydroxypropyl, dihydroxypropyl, methyl, or ethyl.

In one aspect, the invention relates to a pharmaceutical composition wherein said R group is hydroxypropyl. In one aspect, the invention relates to a pharmaceutical composition wherein said hydroxypropyl beta-cyclodextrin has a molecular substitution per anhydro glucose unit of about 0.86 to about 1.14. In one aspect, the invention relates to a pharmaceutical composition wherein said hydroxyl-propyl beta-cyclodextrin has a molecular substitution per anhydro glucose unit of about 0.59 to about 0.73.

In one aspect, the invention relates to a pharmaceutical composition wherein said hydroxypropyl beta-cyclodextrin corresponds to the CAS Registry Number 128446-35-5.

In one aspect, the invention relates to a pharmaceutical composition wherein said cyclodextrin is a sulfoalkyl ether cyclodextrin derivative of Formula 1

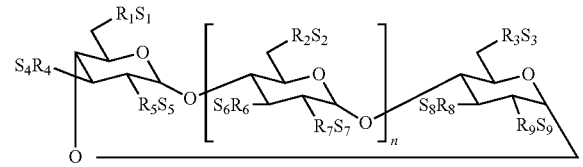

Formula 1 wherein n is 4, 5 or 6;

$R_1$, $R_2$, $R_3$, $R_4$, $R_5$, $R_6$, $R_7$, $R_8$ and $R_9$ in Formula 1 are each, independently, O— or a O—($C_{2-6}$ alkylene)-$SO_3^-$ group, and at least one of $R_1$ and $R_2$ is, independently, said O—($C_{2-6}$ alkylene)-$SO_3^-$ group; and $S_1$, $S_2$, $S_3$, $S_4$, $S_5$, $S_6$, $S_7$, $S_8$ and $S_9$ are each, independently, a pharmaceutically acceptable cation, and wherein said composition shows an absence of underivatized cyclodextrin as measured by thin-layer chromatography. In one aspect, $R_1$, $R_2$ and $R_3$ are each, independently, said O—($C_{2-6}$-alkylene)-$SO_3^-$ group. In one aspect, at least one of $R_1$, $R_2$ and $R_3$ is, independently, a O—$(CH_2)_m$—$SO_3^-$ group, wherein m is 2, 3, 4, 5 or 6. In one aspect, $R_1$, $R_2$ and $R_3$ are each, independently a O—$(CH_2)_m$—$SO_3^-$ group, wherein m is 3 or 4. In one aspect, $R_4$, $R_6$ and $R_8$ is, independently, said O—($C_{2-6}$-alkylene)-$SO_3^-$ group; and $R_5$, $R_7$ and $R_9$ are each —$O^-$. In one aspect, $R_4$, $R_6$ and $R_8$ is, independently, said O—($C_{2-6}$-alkylene)-$SO_3^-$ group; and $R_5$, $R_7$ and $R_9$ are each —$O^-$. In one aspect, $R_4$, $R_6$ and $R_8$ are each a —O—($C_{2-6}$-alkylene)-$SO_3^-$ group; and $R_5$, $R_7$ and $R_9$ are each —$O^-$. In one aspect, $S_1$, $S_2$, $S_3$, $S_4$, $S_5$, $S_6$, $S_7$, $S_8$ and $S_9$ are each, independently, $H^+$, $Li^+$, $Na^+$, $K^+$, $Ca^{+2}$, $Mg^{+2}$, or ammonium.

In one aspect, the invention said sulfoalkyl ether cyclodextrin is sulfobutyl ether beta-cyclodextrin. In one aspect, said sulfoalkyl ether beta-cyclodextrin corresponds to the CAS Registry Number 194615-04-8.

In one aspect, the invention relates to a pharmaceutical composition wherein said cyclodextrin is a gamma-cyclodextrin.

In one aspect, the invention relates to a pharmaceutical composition wherein said quinolone carboxylic acid derivative corresponds to the following structure of Formula 2

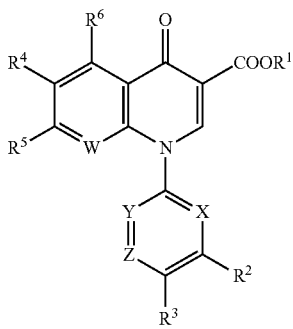

Formula 2 wherein R¹ represents a hydrogen atom or a carboxyl protective group; R² represents a hydroxyl group, a lower alkoxy group, or a substituted or unsubstituted amino group; R³ represents a hydrogen atom or a halogen atom; R⁴ represents a hydrogen atom or a halogen atom; R⁵ represents a halogen atom or an optionally substituted saturated cyclic amino group; R⁶ represents a hydrogen atom, a halogen atom, a nitro group, or an optionally protected amino group; X, Y and Z may be the same or different and respectively represent a nitrogen atom, —CH═ or —CR⁷═ (wherein R⁷ represents a lower alkyl group, a halogen atom, or a cyano group), with the proviso that at least one of X, Y and Z represent a nitrogen atom, and W represents a nitrogen atom or —CR⁸═ (wherein R⁸ represents a hydrogen atom, a halogen atom, or a lower alkyl group); with the proviso that R¹, R², R³, R⁴, R⁵, R⁶, R⁷, R⁸, W, X, Y, and Z are defined with respect to Formula 2, or a pharmaceutically acceptable salt or ester thereof. In one aspect, when R¹ represents a hydrogen atom, R² represents an amino group, R³ and R⁴ represent a fluorine atom, R⁶ represents a hydrogen atom, X represents a nitrogen atom, Y represents —CR⁷═ (wherein R⁷ represents a fluorine atom), Z represents —CH═, and W is —CR⁸═ (wherein R⁸ represents a chlorine atom), then R⁵ is not a 3-hydroxyazetidine-1-yl group, or a pharmaceutically acceptable salt or ester thereof.

In one aspect, the invention relates to a pharmaceutical composition wherein said quinolone carboxylic acid derivative corresponds to the following compound (A)

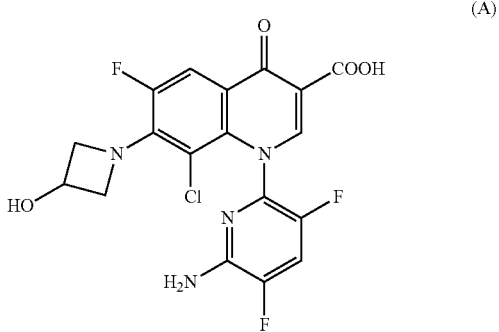 [SMILES: Nc1nc(-n2cc(C(=O)O)c(=O)c3cc(F)c(N4CC(O)C4)c(Cl)c32)c(F)cc1F]

(A)

or a pharmaceutically acceptable salt or ester thereof.

In one aspect, the invention relates to a pharmaceutical composition wherein said quinolone carboxylic acid derivative is a D-glucitol, 1-deoxy-1-(methylamino)-, 1-(6-amino-3,5-difluoro-2-pyridinyl)-8-chloro-6-fluoro-1,4-dihydro-7-(3-hydroxy-1-azetidinyl)-4-oxo-3-quinolinecarboxylate (salt).

In one aspect, the invention relates to a pharmaceutical composition wherein said quinolone carboxylic acid derivative is a crystalline D-glucitol, 1-deoxy-1-(methylamino)-, 1-(6-amino-3,5-difluoro-2-pyridinyl)-8-chloro-6-fluoro-1, 4-dihydro-7-(3-hydroxy-1-azetidinyl)-4-oxo-3-quinolinecarboxylate (salt) characterized, when measured at about 25° C. with Cu-Ka radiation, by the powder diffraction pattern shown in FIG. 1.

In one aspect, the invention relates to a pharmaceutical composition wherein said quinolone carboxylic acid derivative is D-glucitol, 1-deoxy-1-(methylamino)-, 1-(6-amino-3,5-difluoro-2-pyridinyl)-8-chloro-6-fluoro-1,4-dihydro-7-(3-hydroxy-1-azetidinyl)-4-oxo-3-quinolinecarboxylate trihydrate (salt).

Figure 2:
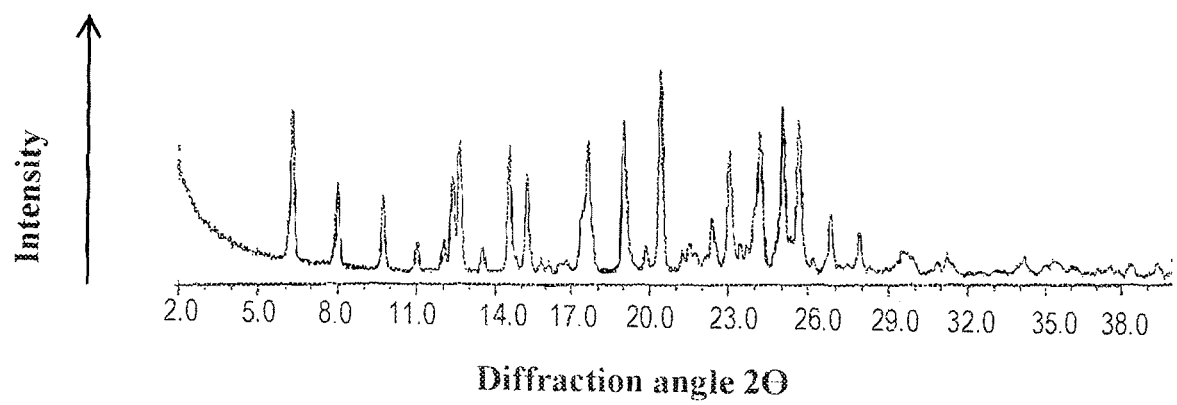
FIG. 2 shows a powder X-ray diffraction pattern of crystalline D-glucitol, 1-deoxy-1-(methylamino)-, 1-(6-amino-3,5-difluoropyridin-2-yl)-8-chloro-6-fluoro-1,4-dihydro-7-(3-h-ydroxyazetidin-1-yl)-4-oxo-3-quinolinecarboxylate trihydrate (salt).

In one aspect, the invention relates to a pharmaceutical composition wherein said quinolone carboxylic acid derivative is crystalline D-glucitol, 1-deoxy-1-(methylamino)-, 1-(6-amino-3,5-difluoro-2-pyridinyl)-8-chloro-6-fluoro-1, 4-dihydro-7-(3-hydroxy-1-azetidinyl)-4-oxo-3-quinolinecarboxylate trihydrate (salt), characterized, when measured at about 25° C. with Cu-Ka radiation, by the powder diffraction pattern shown in FIG. 2.

In one aspect, the invention relates to a pharmaceutical composition wherein said chelating agent is EDTA or a salt thereof. In one aspect, said chelating agent is an EDTA salt selected from the group consisting of a sodium salt, a potassium salt, a calcium salt, a magnesium salt, and mixtures thereof. In one aspect, said chelating agent is disodium EDTA.

In one aspect, the invention relates to a pharmaceutical composition further comprising a polyhydroxyamine compound. In one aspect, said polyhydroxyamine compound is meglumine.

In one aspect, the invention relates to a pharmaceutical composition wherein said quinolone carboxylic acid derivative has a measurable improvement in solubility compared to the quinolone carboxylic acid derivative in water. In one aspect, said quinolone carboxylic acid derivative has a solubility of at least about 1 mg/ml at 25° C. In one aspect, said quinolone carboxylic acid derivative has a solubility of at least about 2 mg/ml at 25° C. In one aspect, quinolone carboxylic acid derivative has a solubility of at least about 3 mg/ml at 25° C. In one aspect, said quinolone carboxylic acid derivative has a solubility of at least about 5 mg/ml at 25° C. In one aspect, said quinolone carboxylic acid derivative has a solubility of at least about 10 mg/ml at 25° C. In one aspect, said quinolone carboxylic acid derivative has a solubility of at least about 15 mg/ml at 25° C. In one aspect, said quinolone carboxylic acid derivative has a solubility of at least about 20 mg/ml at 25° C. In one aspect, said quinolone carboxylic acid derivative has a solubility of at least about 25 mg/ml at 25° C. In one aspect, said quinolone carboxylic acid derivative has a solubility of at least about 30 mg/ml at 25° C.

In one aspect, the invention relates to a pharmaceutical composition which has improved stability.

In one aspect, the invention relates to a pharmaceutical composition having improved stability as measured by at least one of the following parameters:

(a) the composition maintains a pH within about 10% of its initial pH, or (b) the composition retains at least about 90%, or at least 95%, of the initial amount of the quinolone carboxylic acid derivative, or (c) the composition does not form a precipitate such that per unit container, the compositions has 6000 or less particles of 10 microns or greater and has 600 or less particles of 25 microns or greater as measured using a standard light obscuration particle test as described in USP Section 788 on Particulate Matter in Injections.

In one aspect, the invention any of the parameters (a), (b), or (c) are determined at least 30, 69, 90, 180 days, or one year after the composition has been allowed to stand at room temperature, during that time.

In one aspect, the invention relates to a pharmaceutical composition wherein said composition provides a measurable enhancement in venous toleration. In one aspect, said venous toleration is measured in a rat tail infusion model. In one aspect, said composition can be infused in a rat tail infusion model for at least one hour at the rate of 10 ml/kg/hr. In one aspect, the invention relates to a pharmaceutical composition, wherein said composition can be infused on at least two, three, four, or five consecutive days in a rat tail infusion model for at least one hour at the rate of 10 ml/kg/hr.

In one aspect, the invention relates to a pharmaceutical composition, wherein said quinolone carboxylic acid derivative has a measurable improvement in solubility compared to the quinolone carboxylic acid derivative in water, and/or the composition has improved stability, and/or the composition provides a measurable enhancement in venous toleration.

In one aspect, the invention relates to a pharmaceutical composition comprising
 (a) from about 0.01% to about 50% by weight of delafloxacin, as compared to the total weight of the composition;
 (b) from about 0.1% to about 50% by weight of meglumine, as compared to the total weight of the composition; and
 (c) from about 1% to about 50% by weight of sulfobutyl ether beta-cyclodextrin corresponding to the CAS Registry Number 194615-04-8, as compared to the total weight of the composition.

In one aspect, the invention relates to a pharmaceutical composition comprising
 (a) from about 0.01% to about 50% by weight of delafloxacin, as compared to the total weight of the composition;
 (b) from about 0.1% to about 50% by weight of meglumine, as compared to the total weight of the composition;
 (c) from about 1% to about 50% by weight of sulfobutyl ether beta-cyclodextrin corresponding to the CAS Registry Number 194615-04-8, as compared to the total weight of the composition; and
 (d) from about 0.001% to about 0.10% by weight of disodium EDTA, as compared to the total weight of the composition.

In one aspect, the invention relates to a pharmaceutical composition comprising
 (a) from about 100 mg to about 500 mg of delafloxacin,
 (b) from about 15 mg to about 125 mg of meglumine, and
 (c) from about 1000 mg to about 5000 mg of sulfobutyl ether beta-cyclodextrin corresponding to the CAS Registry Number 194615-04-8.

In one aspect, the invention relates to a pharmaceutical composition comprising
 (a) from about 100 mg to about 500 mg of delafloxacin,
 (b) from about 15 mg to about 125 mg of meglumine,
 (c) from about 500 mg to about 5000 mg of sulfobutyl ether beta-cyclodextrin corresponding to the CAS Registry Number 194615-04-8, and
 (d) from 0 mg to about 4 mg disodium EDTA.

In one aspect, the invention relates to a pharmaceutical composition comprising
 (a) from about 100 mg to about 500 mg of delafloxacin,
 (b) from about 15 mg to about 125 mg of meglumine,
 (c) from about 500 mg to about 5000 mg of sulfobutyl ether beta-cyclodextrin corresponding to the CAS Registry Number 194615-04-8, and
 (d) from about 0.40 mg to about 4 mg disodium EDTA.

In one aspect, the invention relates to a pharmaceutical composition comprising
 (a) about 100 mg of delafloxacin,
 (b) about 24.4 mg of meglumine, and
 (c) about 1000 mg of sulfobutyl ether beta-cyclodextrin corresponding to the CAS Registry Number 194615-04-8.

In one aspect, the invention relates to a pharmaceutical composition comprising
 (a) about 300 mg of delafloxacin,
 (b) about 73.2 mg of meglumine, and
 (c) about 3000 mg of sulfobutyl ether beta-cyclodextrin corresponding to the CAS Registry Number 194615-04-8.

In one aspect, the invention relates to a pharmaceutical composition comprising
 (a) about 500 mg of delafloxacin,
 (b) about 122 mg of meglumine, and
 (c) about 5000 mg of sulfobutyl ether beta-cyclodextrin corresponding to the CAS Registry Number 194615-04-8.

In one aspect, the invention relates to a pharmaceutical composition comprising
 (a) about 100 mg of delafloxacin,
 (b) about 19.52 mg of meglumine,
 (c) about 800 mg of sulfobutyl ether beta-cyclodextrin corresponding to the CAS Registry Number 194615-04-8, and
 (d) about 0.44 mg of disodium EDTA.

In one aspect, the invention relates to a pharmaceutical composition comprising
 (a) about 300 mg of delafloxacin,
 (b) about 58.56 mg of meglumine,
 (c) about 2400 mg of sulfobutyl ether beta-cyclodextrin corresponding to the CAS Registry Number 194615-04-8, and
 (d) about 1.32 mg of disodium EDTA.

In one aspect, the invention relates to a pharmaceutical composition comprising
 (a) about 500 mg of delafloxacin,
 (b) about 97.6 mg of meglumine,
 (c) about 4000 mg of sulfobutyl ether beta-cyclodextrin corresponding to the CAS Registry Number 194615-04-8, and
 (d) about 2.2 mg of disodium EDTA In one aspect, the invention relates to an aqueous pharmaceutical composition comprising
 (a) about 20 mg/ml of delafloxacin,
 (b) about 4.88 mg/ml of meglumine,
 (c) about 200 mg/ml of sulfobutyl ether beta-cyclodextrin corresponding to the CAS Registry Number 194615-04-8, and
 (d) water.

In one aspect, the invention relates to an aqueous pharmaceutical composition comprising
 (a) about 25 mg/ml of delafloxacin,
 (b) about 4.88 mg/ml of meglumine, (c) about 200 mg/ml of sulfobutyl ether beta-cyclodextrin corresponding to the CAS Registry Number 194615-04-8,
(d) about 0.11 mg/ml of disodium EDTA, and
(e) water.

In one aspect, the invention relates to any pharmaceutical composition taught above having a pH of about 9±0.1 pH units.

In one aspect, the invention relates to a pharmaceutical composition which further comprises mannitol.

In one aspect, the invention relates to a pharmaceutical composition in the form of a unit dosage.

In one aspect, the invention relates to a method for treating, preventing, or reducing the risk of a bacterial infection comprising administering to a patient in need thereof a composition as taught herein.

In one aspect, the invention relates to a method for treating, preventing, or reducing the risk of a bacterial infection in a patient in need thereof, while reducing venous intoleration during administration, comprising administering to a patient in need thereof a composition as taught herein, e.g. using an i.v. drip bag. The composition can comprise a saline or dextrose carrier.

In one aspect, the invention relates to a kit comprising a pharmaceutical composition and a container. The container can be a bottle, a vial, a syringe or a drip bag, or the composition can further comprise container, e.g. a bottle, a vial, a syringe or a drip bag.

DETAILED DESCRIPTION OF THE INVENTION

In the present invention, it has surpriringly been found that the combination of certain cyclodextrin compounds with a quinolone carboxylic acid derivative antimicrobial compound is found to provide a desired balance of product solubility, stability, and toleration. The final drug product formulation is the result of a complex interplay of solubility, stability, and toleration.

The present invention relates to a pharmaceutical composition comprising a quinolone carboxylic acid derivative or a pharmaceutically acceptable salt or ester thereof, and a cyclodextrin selected from the group consisting of a beta-cyclodextrin, a gamma-cyclodextrin, and mixtures thereof. These compositions are useful for intravenous administration or injection, for treating, preventing, or reducing the risk of infection. These compositions have enhanced stability, enhanced solubility of the quinolone carboxylic acid, and enhanced patient toleration when administered intravenously or as an injection. Enhanced stability is important because a pharmaceutical composition must possess sufficient shelf life to be conveniently stored for a useful period of time. Enhanced solubility is important, because some quinolone carboxylic acid compounds do not have sufficient aqueous solubility to be formulated at a desired target concentration. The present invention provides compositions having enhanced solubility compared to what would otherwise be achievable not employing the present invention. Enhanced patient toleration is important, because the invention provides compositions that are safe and well tolerated. It is not sufficient for a pharmaceutical composition to be efficacious, it is important that efficacy be achieved at an appropriate safety and toleration level. Therefore, the compositions of the present invention provide an advantage over the state of the art.

In one embodiment, the present invention relates to a pharmaceutical composition which prior to mixing comprises (a) a quinolone carboxylic acid derivative or a pharmaceutically acceptable salt or ester thereof, and (b) a cyclodextrin. In other embodiments, the present invention relates to a pharmaceutical composition comprising (a) a quinolone carboxylic acid derivative or a pharmaceutically acceptable salt or ester thereof, and (b) a cyclodextrin. In one embodiment, the composition comprises a quinolone carboxylic acid derivative and a cyclodextrin. In another embodiment, the composition comprises a pharmaceutically acceptable salt of a quinolone carboxylic acid derivative and a cyclodextrin. In another embodiment, the composition comprises a pharmaceutically acceptable ester of a quinolone carboxylic acid derivative and a cyclodextrin. In other embodiments, the present invention relates to a pharmaceutical composition comprising an inclusion complex, said inclusion complex comprising (a) a quinolone carboxylic acid derivative or a pharmaceutically acceptable salt or ester thereof, and (b) a cyclodextrin. In one embodiment, the composition comprises a quinolone carboxylic acid derivative or pharmaceutically acceptable salt or ester thereof within the cyclodextrin.

In other embodiments, the present invention relates to a pharmaceutical composition comprising (that is in the form of) an aqueous solution.

In other embodiments, the present invention relates to a pharmaceutical composition comprising (that is in the form of) a dry mixture. In other embodiments, the present invention relates to a pharmaceutical composition wherein said dry mixture is a lyophile. In other embodiments, the present invention relates to a pharmaceutical composition wherein said dry mixture is made by lyophylization. In other embodiments, the present invention relates to a pharmaceutical composition wherein said dry mixture or lyophile is reconstituted. In other embodiments, the present invention relates to a pharmaceutical composition wherein said pharmaceutical composition is further diluted.

In one embodiment, the present invention relates to a pharmaceutical composition wherein said cyclodextrin is selected from the group consisting of alpha-cyclodextrins, beta-cyclodextrins, gamma-cyclodextrins, and mixtures thereof. In other embodiments, the present invention relates to a pharmaceutical composition wherein said cyclodextrin is selected from the group consisting of beta-cyclodextrins, gamma-cyclodextrins, and mixtures thereof. In one embodiment, the free hydroxyls of the cyclodextrin are completely or partially derivatized. In another embodiment, the free hydroxyls of the cyclodextrin are completely derivatized. In another embodiment, the free hydroxyls of the cyclodextrin are partially derivatized. In other embodiments, the present invention relates to a pharmaceutical composition wherein said cyclodextrin is a beta-cyclodextrin selected from the group consisting of a beta-cyclodextrin ether, a beta-cyclodextrin ester, and mixtures thereof. In other embodiments, the present invention relates to a pharmaceutical composition wherein said cyclodextrin is a hydroxyalkyl-beta-cyclodextrin. In other embodiments, the present invention relates to a pharmaceutical composition wherein said hydroxyalkyl-beta-cyclodextrin is a hydroxypropyl-beta-cyclodextrin. In other embodiments, the present invention relates to a pharmaceutical composition wherein said cyclodextrin is a beta-cyclodextrin corresponding to the following formula (3):

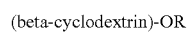

(beta-cyclodextrin)-OR  (3)

in which the residues R are hydroxyalkyl groups and part of the residues R may optionally be alkyl groups, the beta-cyclodextrin ether having a water-solubility of more than 1.8 g in 100 ml water. In other embodiments, the present invention relates to a pharmaceutical composition wherein said cyclodextrin is a beta-cyclodextrin corresponding to the following formula: (beta-cyclodextrin)-OR, in which all or part of the residues R are optionally and independently hydrogen, hydroxyalkyl groups or alkyl groups. In other embodiments, the present invention relates to a pharmaceutical composition wherein said cyclodextrin is a beta-cyclodextrin corresponding to the following formula (3): (beta-cyclodextrin)-OR, in which all or part of the residues R are optionally and independently hydroxyalkyl groups or alkyl groups. In one embodiment, the beta-cyclodextrin has a water-solubility of more than 1.8 g in 100 mL water. In other embodiments, the present invention relates to a pharmaceutical composition wherein R is selected from the group consisting of hydroxyethyl, hydroxypropyl, dihydroxypropyl, methyl, or ethyl. In other embodiments, the present invention relates to a pharmaceutical composition wherein said R group is hydroxypropyl. In other embodiments, the present invention relates to a pharmaceutical composition wherein said hydroxypropyl beta-cyclodextrin has a molecular substitution per anhydro glucose unit of about 0.86 to about 1.14. In other embodiments, the present invention relates to a pharmaceutical composition wherein said hydroxyl-propyl beta-cyclodextrin has a molecular substitution per anhydro glucose unit of about 0.59 to about 0.73. In other embodiments, the present invention relates to a pharmaceutical composition wherein said hydroxypropyl beta-cyclodextrin corresponds to the CAS Registry Number 128446-35-5.

In other embodiments, the present invention relates to a pharmaceutical composition wherein said cyclodextrin is a sulfoalkyl ether cyclodextrin derivative of the formula 1

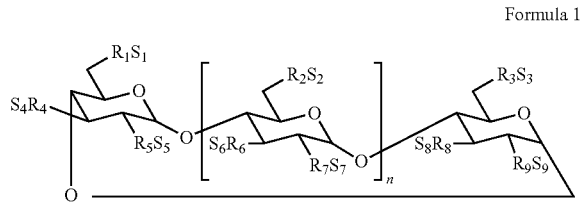

Formula 1 wherein n is 4, 5 or 6; $R_1$, $R_2$, $R_3$, $R_4$, $R_5$, $R_6$, $R_7$, $R_8$ and $R_9$ are each, independently, $O^-$ or a $O$—($C_{2-6}$ alkylene)-$SO_3^-$ group, and at least one of $R_1$ and $R_2$ is, independently, said $O$—($C_{2-6}$ alkylene)-$SO_3^-$ group; and $S_1$, $S_2$, $S_3$, $S_4$, $S_5$, $S_6$, $S_7$, $S_8$ and $S_9$ are each, independently, a pharmaceutically acceptable cation, and wherein said composition shows an absence of underivatized cyclodextrin as measured by thin-layer chromatography. In other embodiments, the present invention relates to a composition, wherein $R_1$, $R_2$ and $R_3$ are each, independently, said $O$—($C_{2-6}$-alkylene)-$SO_3^-$ group. In other embodiments, the present invention relates to a composition, wherein at least one of $R_1$, $R_2$ and $R_3$ is, independently, a $O$—$(CH_2)_m$—$SO_3^-$ group, wherein m is 2, 3, 4, 5 or 6. In other embodiments, the present invention relates to a composition, wherein $R_1$, $R_2$ and $R_3$ are each, independently a $O$—$(CH_2)_m$—$SO_3^-$ group, wherein m is 3 or 4. In other embodiments, the present invention relates to a composition, wherein at least one of $R_4$, $R_6$ and $R_8$ is, independently, said $O$—($C_{2-6}$-alkylene)-$SO_3^-$ group; and $R_5$, $R_7$ and $R_9$ are each $O^-$. In other embodiments, the present invention relates to a composition, wherein at least one of $R_4$, $R_6$ and $R_8$ is, independently, said $O$—($C_{2-6}$-alkylene)-$SO_3^-$ group; and $R_5$, $R_7$ and $R_9$ are each $O^-$. In other embodiments, the present invention relates to a composition, wherein: $R_4$, $R_6$ and $R_8$ are each a $O$—($C_{2-6}$-alkylene)-$SO_3^-$ group; and $R_5$, $R_7$ and $R_9$ are each $O^-$. In other embodiments, the present invention relates to a pharmaceutical composition wherein said sulfoalkyl ether cyclodextrin is sulfobutyl ether beta-cyclodextrin. In other embodiments, the present invention relates to a pharmaceutical composition wherein said sulfoalkyl ether beta-cyclodextrin corresponds to the CAS Registry Number 194615-04-8.

In other embodiments, the present invention relates to a pharmaceutical composition wherein said cyclodextrin is a gamma-cyclodextrin.

In other embodiments, the present invention relates to a composition wherein said quinolone carboxylic acid derivative corresponds to the following structure of Formula 2:

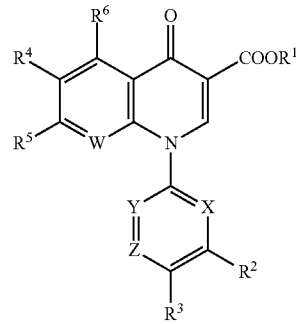

Formula 2 wherein $R^1$ represents a hydrogen atom or a carboxyl protective group; $R^2$ represents a hydroxyl group, a lower alkoxy group, or a substituted or unsubstituted amino group; $R^3$ represents a hydrogen atom or a halogen atom; $R^4$ represents a hydrogen atom or a halogen atom; $R^5$ represents a halogen atom or an optionally substituted saturated cyclic amino group; $R^6$ represents a hydrogen atom, a halogen atom, a nitro group, or an optionally protected amino group; X, Y and Z may be the same or different and respectively represent a nitrogen atom, —CH= or —$CR^7$= (wherein $R^7$ represents a lower alkyl group, a halogen atom, or a cyano group), with the proviso that at least one of X, Y and Z represent a nitrogen atom, and W represents a nitrogen atom or —$CR^8$= (wherein $R^8$ represents a hydrogen atom, a halogen atom, or a lower alkyl group); with the proviso that $R^1$, $R^2$, $R^3$, $R^4$, $R^5$, $R^6$, $R^7$, $R^8$, W, X, Y, and Z as defined as described in this paragraph are defined for Formula 2, and not as defined for the cyclodextrins, or a pharmaceutically acceptable salt or ester thereof.

In one embodiment, when $R^1$ represents a hydrogen atom, $R^2$ represents an amino group, $R^3$ and $R^4$ represent a fluorine atom, $R^6$ represents a hydrogen atom, X represents a nitrogen atom, Y represents —$CR^7$= (wherein $R^7$ represents a fluorine atom), Z represents —CH=, and W is —$CR^8$= (wherein $R^8$ represents a chlorine atom), then $R^5$ is not a 3-hydroxyazetidine-1-yl group;

In other embodiments, the present invention relates to a composition wherein said quinolone carboxylic acid derivative corresponds to the following compound (A),

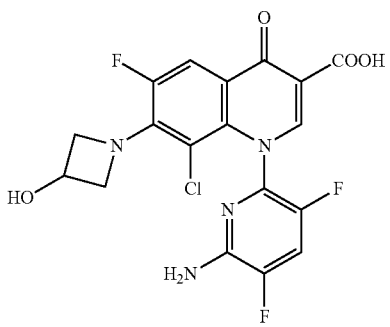

(A)

or a pharmaceutically acceptable salt or ester thereof. In other embodiments, the present invention relates to a composition wherein said quinolone carboxylic acid derivative is a D-glucitol, 1-deoxy-1-(methylamino)-, 1-(6-amino-3,5-difluoro-2-pyridinyl)-8-chloro-6-fluoro-1,4-dihydro-7-(3-hydroxy-1-azetidinyl)-4-oxo-3-quinolinecarboxylate (salt). In other embodiments, the present invention relates to a composition wherein said quinolone carboxylic acid derivative is a crystalline D-glucitol, 1-deoxy-1-(methylamino)-, 1-(6-amino-3,5-difluoro-2-pyridinyl)-8-chloro-6-fluoro-1,4-dihydro-7-(3-hydroxy-1-azetidinyl)-4-oxo-3-quinolinecarboxylate (salt). In yet other embodiments, the present invention relates to a composition wherein said quinolone carboxylic acid derivative is a crystalline D-glucitol, 1-deoxy-1-(methylamino)-, 1-(6-amino-3,5-difluoro-2-pyridinyl)-8-chloro-6-fluoro-1,4-dihydro-7-(3-hydroxy-1-azetidinyl)-4-oxo-3-quinolinecarboxylate (salt) characterized, when measured at about 25° C. with Cu-Ka radiation, by the powder diffraction pattern shown in FIG. 1.

In other embodiments, the present invention relates to a composition wherein said quinolone carboxylic acid derivative is D-glucitol, 1-deoxy-1-(methylamino)-, 1-(6-amino-3,5-difluoro-2-pyridinyl)-8-chloro-6-fluoro-1,4-dihydro-7-(3-hydroxy-1-azetidinyl)-4-oxo-3-quinolinecarboxylate trihydrate (salt). In other embodiments, the present invention relates to a composition wherein said quinolone carboxylic acid derivative is crystalline D-glucitol, 1-deoxy-1-(methylamino)-, 1-(6-amino-3,5-difluoro-2-pyridinyl)-8-chloro-6-fluoro-1,4-dihydro-7-(3-hydroxy-1-azetidinyl)-4-oxo-3-quinolinecarboxylate trihydrate (salt). In yet other embodiments, the present invention relates to a composition wherein said quinolone carboxylic acid derivative is crystalline D-glucitol, 1-deoxy-1-(methylamino)-, 1-(6-amino-3,5-difluoro-2-pyridinyl)-8-chloro-6-fluoro-1,4-dihydro-7-(3-hydroxy-1-azetidinyl)-4-oxo-3-quinolinecarboxylate trihydrate (salt) characterized, when measured at about 25° C. with Cu-Ka radiation, by the powder diffraction pattern shown in FIG. 2.

In other embodiments, the present invention relates to a composition wherein said quinolone carboxylic acid derivative has a measurable improvement in solubility. In other embodiments, the present invention relates to a composition wherein said quinolone carboxylic acid derivative has a measurable improvement in solubility compared to the quinolone carboxylic acid derivative alone in water.

In other embodiments, the present invention relates to a composition wherein said quinolone carboxylic acid derivative has a solubility of at least about 1 mg/ml at 25° C. In other embodiments, the present invention relates to a composition wherein said quinolone carboxylic acid derivative has a solubility of at least about 2 mg/ml at 25° C. In other embodiments, the present invention relates to a composition wherein said quinolone carboxylic acid derivative has a solubility of at least about 3 mg/ml at 25° C. In other embodiments, the present invention relates to a composition wherein said quinolone carboxylic acid derivative has a solubility of at least about 5 mg/ml at 25° C. In other embodiments, the present invention relates to a composition wherein said quinolone carboxylic acid derivative has a solubility of at least about 10 mg/ml at 25° C. In other embodiments, the present invention relates to a composition wherein said quinolone carboxylic acid derivative has a solubility of at least about 15 mg/ml at 25° C. In other embodiments, the present invention relates to a composition wherein said quinolone carboxylic acid derivative has a solubility of at least about 20 mg/ml at 25° C. In other embodiments, the present invention relates to a composition wherein said quinolone carboxylic acid derivative has a solubility of at least about 25 mg/ml at 25° C. In other embodiments, the present invention relates to a composition wherein said quinolone carboxylic acid derivative has a solubility of at least about 30 mg/ml at 25° C.

In other embodiments, the present invention relates to a composition which has improved stability. In other embodiments, the present invention relates to a composition which has improved stability as measured by at least one of the following parameters: (a) the composition maintains a pH within about 10% of its initial pH, or (b) the composition retains at least about 90%, or 95%, of the initial amount of the quinolone carboxylic acid derivative, or (c) the composition does not form a precipitate such that per unit container, the compositions has 6000 or less particles of 10 microns or greater and has 600 or less particles of 25 microns or greater as measured using a standard light obscuration particle test as described in USP Section 788 on Particulate Matter in Injections.

The pharmaceutical compositions of the invention have sufficient chemical and physical stability to enable administration to a patient and maintain efficacy of the pharmaceutical active over a useful length of time. In one embodiment, in the pharmaceutical composition, the potency of the quinoline carboxylic acid derivative active ingredient is maintained by retaining the pharmaceutical active in solution, by limiting chemical degradation of the pharmaceutical active or other components of the pharmaceutical composition, or by limiting physical degradation of the composition. In one embodiment, the composition retains the solubility of the drug, the drug efficacy, or protects the drug or components of the composition from chemical or physical degradation. In another embodiment, the composition retains the drug potency of the initial formulation, or a potency substantially similar to the initial formulation.

In other embodiments, the present invention relates to a composition wherein any of the parameters (a), (b), or (c) are determined at least 30 days after the composition has been allowed to stand at room temperature. In other embodiments, the present invention relates to a composition wherein any of the parameters (a), (b), or (c) are determined at least 60 days after the composition has been allowed to stand at room temperature. In other embodiments, the present invention relates to a composition wherein any of the parameters (a), (b), or (c) are determined at least 90 days after the composition has been allowed to stand at room temperature. In other embodiments, the present invention relates to a composition wherein any of the parameters (a), (b), or (c) are determined at least 180 days after the composition has been allowed to stand at room temperature. In other embodiments, the present invention relates to a composition wherein any of the parameters (a), (b), or (c) are determined at least 1 year after the composition has been allowed to stand at room temperature.

In other embodiments, the present invention relates to a composition wherein said composition provides a measurable enhancement in venous toleration. In other embodiments, the present invention relates to a composition wherein said venous toleration is measured in a rat tail infusion model. In other embodiments, the present invention relates to a composition wherein said composition can be infused in a rat tail infusion model for at least one hour at the rate of 10 ml/kg/hr.

In other embodiments, the present invention relates to a composition wherein said composition can be infused on at least two consecutive days in a rat tail infusion model for at least one hour at the rate of 10 ml/kg/hr. In other embodiments, the present invention relates to a composition wherein said composition can be infused on at least three consecutive days in a rat tail infusion model for at least one hour at the rate of 10 ml/kg/hr. In other embodiments, the present invention relates to a composition wherein said composition can be infused on at least four consecutive days in a rat tail infusion model for at least one hour at the rate of 10 ml/kg/hr. In other embodiments, the present invention relates to a composition wherein said composition can be infused on at least five consecutive days in a rat tail infusion model for at least one hour at the rate of 10 ml/kg/hr.

In other embodiments, the present invention relates to a composition wherein said quinolone carboxylic acid derivative has a measurable improvement in solubility compared to the quinolone carboxylic acid derivative in water, and/or the composition has improved stability, and/or the composition provides a measurable enhancement in venous toleration.

In other embodiments, the present invention relates to a pharmaceutical composition comprising (a) from about 100 mg to about 500 mg of delafloxacin meglumine, and (b) from about 1000 mg to about 5000 mg of sulfobutyl ether beta-cyclodextrin corresponding to the CAS Registry Number 194615-04-8. In other embodiments, the present invention relates to a pharmaceutical composition comprising (a) about 300 mg of delafloxacin meglumine, and (b) about 3000 mg of sulfobutyl ether beta-cyclodextrin corresponding to the CAS Registry Number 194615-04-8. In other embodiments, the present invention relates to a pharmaceutical composition which prior to mixing comprises (a) about 300 mg of delafloxacin meglumine, and (b) about 3000 mg of sulfobutyl ether beta-cyclodextrin corresponding to the CAS Registry Number 194615-04-8.

In other embodiments, the present invention relates to an aqueous pharmaceutical composition comprising (a) about 300 mg of delafloxacin meglumine, (b) about 3000 mg of sulfobutyl ether beta-cyclodextrin corresponding to the CAS Registry Number 194615-04-8, and (c) water, wherein said composition has a volume at about 25° C. of about 15 ml and a pH of about 9. In other embodiments, the present invention relates to a composition which is in the form of a lyophile. In other embodiments, the present invention relates to a composition which further comprises mannitol.

In other embodiments, the present invention relates to a method for treating, preventing, or reducing the risk of a bacterial infection comprising administering to a patient in need thereof a composition as described herein. In other embodiments, the present invention relates to a method for treating, preventing, or reducing the risk of a bacterial infection in a patient in need thereof, while reducing discomfort upon infusion, comprising administering to a patient in need thereof a composition as described herein.

1. Definitions

The term "patient", as used herein, means the human or animal (in the case of an animal, more typically a mammal) subject. The patient is usually one that is in need of the compositions or methods described herein. "In need of," can mean that the patient has or is diagnosed as having an infection, e.g. a microbial infection, or that the patient is at risk of contracting an infection due to an injury, a medical or surgical procedure, or microbial exposure, or could be in a position that could subject the patient to such exposure. Such infections can be due to, e.g., a skin infection, nosocomial pneumonia, post-viral pneumonia, an abdominal infection, a urinary tract infection, bacteremia, septicemia, endocarditis, an atrio-ventricular shunt infection, a vascular access infection, meningitis, infection due to surgical or invasive medical procedures, a peritoneal infection, a bone infection, a joint infection, a methicillin-resistant *Staphylococcus aureus* infection, a vancomycin-resistant Enterococci infection, a linezolid-resistant organism infection, tuberculosis, a quinolone resistant Gram-positive infection, a ciprofloxacin resistant methicillin resistant (MRSA) infection, bronchitis, a complicated skin and skin structure infection (cSSSI), an uncomplicated skin and skin structure infection (uSSSI), a community respiratory-tract infection, and a multi drug resistant (MDR) Gram-negative infection.

The term "preventing", as used herein, means e.g., to completely or almost completely stop an infection from occurring, for example when the patient is predisposed to an infection or at risk of contracting an infection.

The term "reducing the risk of", as used herein means, e.g. to lower the likelihood or probability of an infection occurring, for example when the patient is predisposed to an infection or at risk of contracting an infection.

The term "treating" as used herein means, e.g. to cure, inhibit, arrest the development, relieve the symptoms or effects of, ameliorating, or cause the regression of an infection in a patient having an infection.

It should be recognized that the terms "preventing", "reducing the risk of", and "treating" are not intended to limit the scope of the invention and that there can be overlap amongst these terms.

As used herein, the term "effective amount" means an amount of a pharmaceutically active compound, i.e. a drug active, e.g. a quinolone carboxylic acid antimicrobial agent or pharmaceutically acceptable salt or ester thereof, given to a recipient patient sufficient to elicit biological activity, for example, anti-infective activity, e.g., anti-microbial activity.

The term "prophylactically effective amount" means an amount of a pharmaceutically active compound, i.e. a drug active, e.g. a quinolone carboxylic acid antimicrobial agent given to a recipient patent sufficient to prevent or reduce the risk of a microbial infection.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

The pharmaceutically acceptable salts of the present invention can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. In one embodiment, non-aqueous media, for example ether, ethyl acetate, ethanol, isopropanol, or acetonitrile are useful for forming salts of the present compounds. Lists of suitable salts are found in *Remington's Pharmaceutical Sciences*, 18$^{th}$ ed. (Mack Publishing Company, 1990). For example, salts can include, but are not limited to, the hydrochloride and acetate salts of the aliphatic amine-containing, hydroxyl amine-containing, and imine-containing compounds of the present invention.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

As used herein, "pharmaceutically acceptable esters" refer to derivatives of the disclosed compounds wherein the parent compound is modified by an alcohol ester of a carboxylic acid or a carboxylic acid ester of an alcohol. The compounds of the present invention can also be prepared as esters, for example pharmaceutically acceptable esters. For example a carboxylic acid function group in a compound can be converted to its corresponding ester, e.g., a methyl, ethyl, or other ester. Also, an alcohol group in a compound can be converted to its corresponding ester, e.g., an acetate, propionate, or other ester.

As used herein, the term "unit dosage", means a single dose of a pharmaceutical composition that is intended to be administered in its entirety. A unit dosage is a convenient form for administering a premeasured amount of a drug active.

In the specification, the singular forms also include the plural, unless the context clearly dictates otherwise. Unless defined otherwise, all technical and scientific terms used herein have the same meaning as commonly understood by one of ordinary skill in the art to which this invention belongs. In the case of conflict, the present specification will control.

All percentages and ratios used herein, unless otherwise indicated, are by weight.

Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

2. Compositions of the Present Invention

The compositions of the present invention comprise all or some of the following components. The compositions can be defined either prior to or after mixing of the components.

Suitable components are described in e.g., Eds. R. C. Rowe, et al., Handbook of Pharmaceutical Excipients, Fifth Edition, Pharmaceutical Press (2006); *Remington's Pharmaceutical Sciences*, 18$^{th}$ ed. (Mack Publishing Company, 1990); and *Remington: The Science and Practice of Pharmacy*, 20$^{th}$ Edition, Baltimore, MD: Lippincott Williams & Wilkins, 2000, which are incorporated by reference herein in their entirety. Even though a functional category can be provided for many of these carrier components, such a functional category is not intended to limit the function or scope of the component, as one of ordinary skill in the art will recognize that a component can belong to more than one functional category and that the level of a specific component and the presence of other components can effect the functional properties of a component.

a. Quinolone Carboxylic Acid Derivative

The compositions of the present invent comprise a quinolone carboxylic acid derivative, (alternatively known as, inter alia, a pyridonecarboxylic acid derivative or a pyridone carboxylic acid derivative), or a pharmaceutically acceptable salt or ester thereof, as an antimicrobial compound, i.e. as the active pharmaceutical ingredient, or API, of the compositions of the present invention. The invention further provides methods for synthesizing any one of the compounds of the present invention. The invention also provides pharmaceutical compositions comprising an effective amount of one or more of the compounds of the present invention and a pharmaceutically acceptable carrier. The present invention further provides methods for making these compounds, carriers, and pharmaceutical compositions.

Quinolone carboxylic acid derivatives, useful herein are described, including their syntheses, formulation, and use, in U.S. Pat. No. 6,156,903, to Yazaki et al., issued Dec. 5, 2000 and its certificates of correction of Nov. 13, 2001 and Dec. 11, 2001; U.S. Pat. No. 6,133,284, to Yazaki et al., issued Oct. 17, 2000; U.S. Pat. No. 5,998,436, to Yazaki et al., issued Dec. 7, 1999 and its certificates of correction of Jan. 23, 2001, Oct. 30, 2001, and Dec. 17, 2002; PCT Application No. WO 2006/110815, to Abbott Laboratories, published Oct. 19, 2006; PCT Application No. WO 2006/042034, to Abbott Laboratories, published Apr. 20, 2006, PCT Application No. WO 2006/015194, to Abbott Laboratories, published Feb. 9, 2006; PCT Application No. WO 01/34595, to Wakunaga Pharmaceutical Co., Ltd., published May 17, 2001; and PCT Application No. WO 97/11068, to Wakunaga Pharmaceutical Co., Ltd., published Mar. 27, 1997, the contents of each of which are hereby incorporated by reference in their entireties.

Quinolone carboxylic acid derivatives useful in the methods, compositions, and uses of the present invention include compounds corresponding to Formula 2

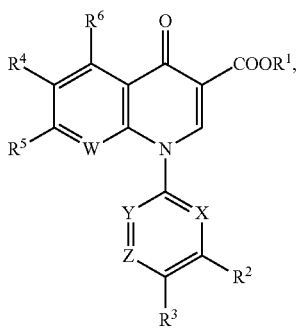

Formula 2 wherein with respect to Formula 2, $R^1$ represents a hydrogen atom or a carboxyl protective group; $R^2$ represents a hydroxyl group, a lower alkoxy group, or a substituted or unsubstituted amino group; $R^3$ represents a hydrogen atom or a halogen atom; $R^4$ represents a hydrogen atom or a halogen atom; $R^5$ represents a halogen atom or an optionally substituted saturated cyclic amino group; $R^6$ represents a hydrogen atom, a halogen atom, a nitro group, or an optionally protected amino group; X, Y and Z may be the same or different and respectively represent a nitrogen atom, —CH= or —CR$^7$= (wherein $R^7$ represents a lower alkyl group, a halogen atom, or a cyano group), with the proviso that at least one of X, Y and Z represent a nitrogen atom, and W represents a nitrogen atom or —CR$^8$=(wherein R represents a hydrogen atom, a halogen atom, or a lower alkyl group).

In one embodiment, when $R^1$ represents a hydrogen atom, $R^2$ represents an amino group, $R^3$ and $R^4$ represent a fluorine atom, $R^6$ represents a hydrogen atom, X represents a nitrogen atom, Y represents —CR$^7$= (wherein $R^7$ represents a fluorine atom), Z represents —CH=, and W is —CR$^8$= (wherein R represents a chlorine atom), then R is not a 3-hydroxyazetidine-1-yl group; or a pharmaceutically acceptable salt, ester, or prodrug thereof.

When $R^1$ is a carboxyl protective group, it may be any carboxylate ester residue which cleaves relatively easily, such as in vivo, to generate the corresponding free carboxyl group. Exemplary carboxyl protective groups include those which may be eliminated by hydrolysis, catalytic reduction, and other treatments under mild conditions such as lower alkyl groups such as methyl group, ethyl group, n-propyl group, i-propyl group, n-butyl group, i-butyl group, t-butyl group, pentyl group, hexyl group, and heptyl group; lower alkenyl groups such as vinyl group, allyl group, 1-propenyl group, butenyl group, pentenyl group, hexenyl group, and heptenyl group; aralkyl groups such as benzyl group; and aryl groups such as phenyl group and naphthyl group; and those which may be readily eliminated in the body such as lower alkanoyloxy lower alkyl groups such as acetoxymethyl group and pivaloyloxymethyl group; lower alkoxycarbonyloxy lower alkyl group such as methoxycarbonyloxymethyl group and 1-ethoxycarbonyloxyethyl group; lower alkoxymethyl group such as methoxymethyl group; lactonyl group such as phthalidyl; di-lower alkylamino lower alkyl group such as 1-dimethylaminoethyl group; and (5-methyl-2-oxo-1,3-dioxole-4-yl)methyl group.

In one embodiment, $R^1$ in Formula 2 is H.
In one embodiment, $R^2$ in Formula 2 is —NH$_2$.
In one embodiment, $R^3$ in Formula 2 is halogen.
In another embodiment, $R^3$ in Formula 2 is fluorine.
In one embodiment, $R^4$ in Formula 2 is halogen.
In another embodiment, $R^4$ in Formula 2 is fluorine.
In one embodiment, $R^5$ in Formula 2 is a substituted cyclic amino group.
In one embodiment, $R^5$ in Formula 2 is

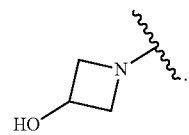

In one embodiment, $R^6$ in Formula 2 is hydrogen.
In one embodiment, X in Formula 2 is a nitrogen atom.
In one embodiment, Y in Formula 2 is =CR$^7$—.
In one embodiment, $R^7$ in Formula 2 is a halogen.
In another embodiment, $R^7$ in Formula 2 is fluorine.
In one embodiment, Z in Formula 2 is =CH—.
In one embodiment, W in Formula is 2 =CR$^8$—.
In one embodiment, $R^8$ in Formula 2 is a halogen.
In another embodiment, $R^8$ in Formula 2 is chlorine.

It is noted that the substituents $R^1$, $R^2$, $R^3$, $R^4$, $R^5$, $R^6$, $R^7$, $R^8$, $R^9$, A, $J^1$, $J^2$, $J^3$, W, X, Y, Z, e, f, and g are defined herein for convenience with respect to the chemical structure for the quinolone carboxylic acid derivatives, for example for Formula 2.

In other embodiments, the present invention relates to a method, composition, or use for a compound of Formula 2, wherein W is —CR$^8$=, wherein $R^8$ represents a hydrogen atom, a halogen atom, or a lower alkyl group.

In other embodiments, the present invention relates to a method, composition, or use for a quinolone carboxylic acid derivative of Formula 2, wherein $R^5$ is a group represented by the following formula (a) or (b):

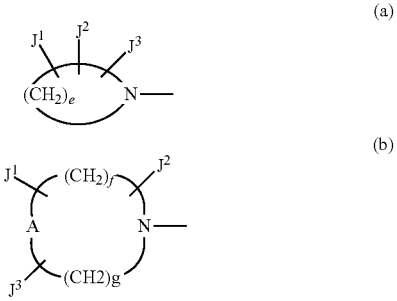

wherein A represents an oxygen atom, sulfur atom or NR$^9$ (wherein $R^9$ represents hydrogen atom or a lower alkyl group), e represents a number from 3 to 5, f represents a number from 1 to 3, g represents a number from 0 to 2, $J^1$, $J^2$ and $J^3$, which may be the same or different from one another, represent a hydrogen atom, hydroxyl group, lower alkyl group, amino lower alkyl group, amino group, lower alkylamino group, lower alkoxy group, or a halogen atom.

In other embodiments, the present invention relates to a method, composition, or use for a quinolone carboxylic acid derivative of Formula 2, wherein $R^5$ is a group represented by formula (a).

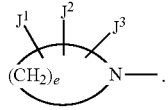

(a)

In other embodiments, the present invention relates to a method, composition, or use for a quinolone carboxylic acid derivative of structure Quinolone Carboxylic Acid Derivative 1, wherein e in the formula (a) is 3 or 4.

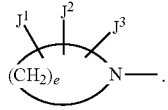

(a)

In other embodiments, the present invention relates to a method, composition, or use for a quinolone carboxylic acid derivative of structure Quinolone Carboxylic Acid Derivative 1, wherein $R^1$ is a hydrogen atom; $R^2$ is an amino group, lower alkylamino group, or a di-lower alkylamino group; $R^3$ is a halogen atom; $R^4$ is a halogen atom; $R^6$ is hydrogen atom; X is a nitrogen atom; Y and Z are —CH= or —CR$^7$= (wherein $R^7$ is a lower alkyl group or a halogen atom); and W is —CR$^8$= (wherein $R^8$ is a halogen atom or a lower alkyl group).

In other embodiments, the present invention relates to a method, composition, or use for a quinolone carboxylic acid derivative of structure Quinolone Carboxylic Acid Derivative 1, wherein $R^2$ is amino group; $R^3$ is fluorine atom; $R^4$ is a fluorine atom; Y is —CF=; Z is —CH=; W is —CR$^8$= (wherein R is a chlorine atom, bromine atom or a methyl group), and e in formula (a) is 3.

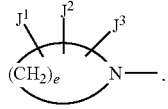

(a)

It should be noted that the variables used to describe the quinolone carboxylic acid derivatives are intended to be separate from the variables used to define the cyclodextrins.

In other embodiments, the present invention relates to a method, composition, or use wherein said quinolone carboxylic acid corresponds to the compound (A):

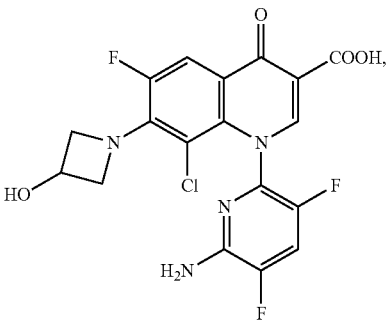

(A)

or a pharmaceutically acceptable salt, ester, or prodrug thereof. This foregoing quinolone carboxylic acid derivative, compound (A), is also known by the USAN, delafloxacin, the publicly disclosed code names RX-3341, ABT-492 and WQ 3034, and also by, inter alia, the chemical name 1-(6-amino-3,5-difluoro-2-pyridinyl)-8-chloro-6-fluoro-1, 4-dihydro-7-(3-hydroxy-1-azetidinyl)-4-oxo-3-quinolinecarboxylic acid or 1-(6-amino-3,5-difluoro-2-pyridinyl)-8-chloro-6-fluoro-1,4-dihydro-7-(3-hydroxyazetidin-1-yl)-4-oxo-3-quinolinecarboxylic acid. This carboxylic acid form of the compound corresponds to the CAS Registry Number 189279-58-1. Furthermore, WO 2006/042034, cited above discloses the 1-deoxy-1-(methylamino)-D-glucitol salt of this compound, also known as D-glucitol, 1-deoxy-1-(methylamino)-, 1-(6-amino-3,5-difluoro-2-pyridinyl)-8-chloro-6-fluoro-1,4-dihydro-7-(3-hydroxy-1-azetidinyl)-4-oxo-3-quinolinecarboxylate (salt), and the trihydrate of the 1-deoxy-1-(methylamino)-D-glucitol salt of this compound, also known as D-glucitol, 1-deoxy-1-(methylamino)-, 1-(6-amino-3,5-difluoro-2-pyridinyl)-8-chloro-6-fluoro-1,4-dihydro-7-(3-hydroxy-1-azetidinyl)-4-oxo-3-quinolinecarboxylate trihydrate (salt). The 1-deoxy-1-(methylamino)-D-glucitol salt and the 1-deoxy-1-(methylamino)-D-glucitol salt trihydrate correspond to the CAS Registry Numbers 352458-37-8 and 883105-02-0, respectively. 1-Deoxy-1-(methylamino)-D-glucitol corresponds to the CAS Registry Number 6284-40-8. 1-Deoxy-1-(methylamino)-D-glucitol is also known by the name meglumine. D-glucitol, 1-deoxy-1-(methylamino)-, 1-(6-amino-3,5-difluoro-2-pyridinyl)-8-chloro-6-fluoro-1,4-dihydro-7-(3-hydroxy-1-azetidinyl)-4-oxo-3-quinolinecarboxylate, which is the meglumine salt of delafloxacin, is also known as delafloxacin meglumine. D-glucitol, 1-deoxy-1-(methylamino)-, 1-(6-amino-3,5-difluoro-2-pyridinyl)-8-chloro-6-fluoro-1,4-dihydro-7-(3-hydroxy-1-azetidinyl)-4-oxo-3-quinolinecarboxylate trihydrate, which is the trihydrate of the meglumine salt of delafloxacin, is also known as delafloxacin meglumine trihydrate. WO 2006/042034 also discloses a crystalline form of the 1-deoxy-1-(methylamino)-D-glucitol salt characterized when measured at about 25° C. with Cu-Ka radiation, by the powder diffraction pattern shown in FIG. 1 (see WO 2006/042034) and a crystalline form of the 1-deoxy-1-(methylamino)-D-glucitol salt trihydrate when measured at about 25° C. with Cu-Ka radiation, by the powder diffraction pattern shown in FIG. 2 (see WO 2006/042034, which is hereby incorporated by reference in its entirety). These 1-deoxy-1-(methylamino)-D-glucitol salts are useful in the present invention. Also, see A. R. Haight et al., "Synthesis of the Quinolone ABT-492: Crystallizations for Optimal Processing", Organic Process Research & Development (2006), 10(4), 751-756, which is hereby incorporated by reference in its entirety.

Additionally other pharmaceutically acceptable salts of the forgoing compound, delafloxacin, include the potassium salt and the tris salt. Tris is a common abbreviation for tris(hydroxymethyl)aminomethane, which is known by the IUPAC name 2-Amino-2-hydroxymethyl-propane-1,3-diol.

The quinolone carboxylic acid antimicrobial agent comprises from about 0.01% to about 50% by weight of the composition. In further embodiments, the quinolone carboxylic acid antimicrobial agent comprises from about 0.25% to about 20% by weight of the composition. In yet further embodiments, the quinolone carboxylic acid antimicrobial agent comprises from about 0.5% to about 10% by weight of the composition. In yet further embodiments, the quinolone carboxylic acid antimicrobial agent comprises from about 1% to about 5% by weight of the composition. The weight percentage of the quinolone carboxylic acid antimicrobial agent is determined on an active weight basis of the parent compound. In other words, appropriate adjustments and calculations well known to one of ordinary skill in the art can be readily performed to determine the active weight basis. As a nonlimiting example, if the parent free carboxylic acid of delafloxacin, i.e. 1-(6-amino-3,5-difluoro-2-pyridinyl)-8-chloro-6-fluoro-1,4-dihydro-7-(3-hydroxy-1-azetidinyl)-4-oxo-3-quinolinecarboxylic acid, is used, its weight would have to be adjusted if a salt such as the sodium salt were to be used, because the molecular weight of the compound would increase by about 21.9, although the amount of active compound delivered is the same.

The dose of the pharmaceutical active and mode of administration of the pharmaceutical composition will depend upon the intended patient or subject and the targeted microorganism, e.g., the target bacterial organism.

As further described below, it is often advantageous to mill the pharmaceutical active to a small and uniform particle size, usually in the micron range, i.e. micronization. Milling can be performed using standard techniques well known to one of ordinary skill in the art. In one embodiment, useful particle size ranges for the pharmaceutical active are generally from about 0.01 microns to about 100 microns. In another embodiment, useful particle size ranges for the pharmaceutical active are from about 0.1 microns to about 20 microns. In another embodiment, useful particle size ranges for the pharmaceutical active are from about 0.5 microns to about 5 microns.

b. Cyclodextrins

The compositions of the present invention comprise a cyclodextrin (sometimes abbreviated as "CD"). Cyclodextrins are cyclic oligosaccharides composed of five or more alpha-D-glucopyranoside units, i.e. sugar units. Cyclodextrins are produced from starch by means of enzymatic conversion. Cyclodextrins having six sugar units are referred to as alpha-cyclodextrins (also "α-cyclodextrins"). Cyclodextrins having seven sugar units are referred to as beta-cyclodextrins (also "β-cyclodextrins"). Cyclodextrins having eight sugar units are referred to as gamma-cyclodextrins (also "γ-cyclodextrins"). Cyclodextrins are further described in the *Handbook of Pharmaceutical Excipients*, Third Edition, Edited by A. H. Kibbe, pages 165-168, American Pharmaceutical Association and Pharmaceutical Press (2000), which are incorporated by reference herein in there entirety.

Cyclodextrins, which are cyclic oligosaccharides, have been reported for use in pharmaceutical formulations. Also, publications in the field of pharmaceutical product development have reported various formulations and technologies relating to drug solubility and stability, and also to tolerability of intravenous formulations. See, for example, U.S. Pat. No. 6,407,079 B1, to Muller et al., issued Jun. 18, 2002; U.S. Pat. No. 5,874,418, to Stella et al., issued Feb. 23, 1999; U.S. Pat. No. 5,376,645, to Stella et al., issued Dec. 27, 1994; U.S. Pat. No. 5,134,127, to Stella et al., issued Jul. 28, 1992; and U.S. Pat. No. 5,084,276, to Yunker et al., issued Jan. 28, 1992, each of which is hereby incorporated by reference in its entirety.

However, although cyclodextrins have been taught as excipients for formulating pharmaceutical compositions for intravenous administration, not all cyclodextrins are automatically useable to provide the desired formulation characteristics and benefits. Based on what is taught in the literature, one cannot apriori select a cyclodextrin for use with a particular drug product to obtain the desired end result. The final drug product formulation is the result of a complex interplay of solubility, stability, and toleration.

The cyclodextrin comprises from about 0.01% to about 50% by weight of the composition. In further embodiments, the quinolone carboxylic acid antimicrobial agent comprises from about 0.25% to about 20% by weight of the composition.

In one embodiment, the compositions of the present invention comprise a cyclodextrin selected from the group consisting of an alpha-cyclodextrin, a beta-cyclodextrin, a gamma-cyclodextrin, and mixtures thereof. In one embodiment, the compositions of the present invention comprise a cyclodextrin selected from the group consisting of a beta-cyclodextrin, a gamma-cyclodextrin, and mixtures thereof.

Beta-cyclodextrins useful herein comprise beta-cyclodextrin ethers, beta-cyclodextrin esters, and mixtures thereof. Beta-cyclodextrins are further described in U.S. Pat. No. 6,407,079, to Muller et al., issued Jun. 18, 2002, which is incorporated by reference herein in its entirety. This '079 patent describes these beta-cyclodextrins as corresponding to the following formula (3):

$$\text{(beta-Cyclodextrin)-OR} \qquad (3)$$

in which the residues R are hydrogen or hydroxyalkyl groups and part of the residues R may optionally be alkyl groups, the beta-cyclodextrin ether having a water-solubility of more than 1.8 g in 100 ml water. In one embodiment, the residues R are hydroxyalkyl groups and part of the residues R may optionally be alkyl groups. In another embodiment, the beta-cyclodextrin ether having a water-solubility of more than 1.8 g in 100 ml water. In still another embodiment, the residues R are hydroxyalkyl groups and part of the residues R may optionally be alkyl groups, the beta-cyclodextrin ether having a water-solubility of more than 1.8 g in 100 ml water.

In one embodiment, a partially etherified beta-cyclodextrin of formula 3 is used in which some of the residues R are hydroxyethyl, hydroxypropyl or dihydroxypropyl groups. Optionally part of the residues R may for instance be methyl or ethyl groups. In one embodiment, the use of partially methylated beta-cyclodextrin ethers with 7 to 14 methyl groups in the beta-cyclodextrin molecule, as they are known from German Offenlegungsschrift 31 18 218 do not come under the present invention. In one embodiment, partial ethers of beta-cyclodextrin comprising only alkyl groups (methyl, ethyl) may be suitable in accordance with the invention if they have a low degree of substitution (as defined below) of 0.05 to 0.2.

Beta-cyclodextrin is a compound with ring structure consisting of 7 anhydro glucose units; it is also referred to as cycloheptaamylose. Each of the 7 glucose rings contains in 2-, 3-, and 6-position three hydroxy groups which may be etherified. In the partially etherified beta-cyclodextrin derivatives used according to the invention only part of these hydroxy groups is etherified with hydroxyalkyl groups and optionally further with alkyl groups. When etherifying with hydroxy alkyl groups which can be carried out by reaction with the corresponding alkylene oxides, the degree of substitution is stated as molar substitution (MS), viz. in mole alkylene oxide per anhydroglucose unit, compare U.S. Pat. No. 3,459,731, column 4. In the hydroxyalkyl ethers of beta-cyclodextrin used in accordance with the invention the molar substitution is between 0.05 and 10. In another embodiment, the molar substitution is between 0.2 and 2. In another embodiment, the molar substitution is about 0.25 to about 1.

The etherification with alkyl groups may be stated directly as degree of substitution (DS) per glucose unit which—as stated above—is 3 for complete substitution. Partially etherified beta-cyclodextrins are used within the invention which comprise besides hydroxyalkyl groups also alkyl groups, especially methyl or ethyl groups, up to a degree of substitution of 0.05 to 2.0. In one embodiment, the degree of substitution with alkyl groups is between 0.2 to 1.5. In one embodiment, the degree of substitution with alkyl groups is between about 0.5 and about 1.2.

In one embodiment, the molar ratio of drug to beta-cyclodextrin ether is about 1:6 to 4:1, especially about 1:2 to 1:1. In one embodiment, the complex forming agent is used in a molar excess.

Useful complex forming agents are especially the hydroxyethyl, hydroxypropyl and dihydroxypropyl ether, their corresponding mixed ethers, and further mixed ethers with methyl or ethyl groups, such as methyl-hydroxyethyl, methyl-hydroxypropyl, ethyl-hydroxyethyl and ethyl-hydroxypropyl ether of beta-cyclodextrin.

The preparation of the hydroxyalkyl ethers of beta-cyclodextrin may be carried out using the method of U.S. Pat. No. 3,459,731. Suitable preparation methods for beta-cyclodextrin ethers may further be found in J. Sziejtli et al., Starke 32, 165 (1980) and A. P. Croft and R. A. Bartsch, Tetrahedron 39, 1417 (1983). Mixed ethers of beta-cyclodextrin can be prepared by reacting beta-cyclodextrin in a basic liquid reaction medium comprising an akali metal hydroxide, water and optionally at least one organic solvent (e.g. dimethoxyethane or isopropanol) with at least two different hydroxyalkylating and optionally alkylating etherifying agents (e.g. ethylene oxide, propylene oxide, methyl or ethyl chloride).

Beta-cyclodextrins useful herein include hydroxypropyl-beta-cyclodextrins.

Examples of hydroxypropyl-beta-cyclodextrins useful herein include Cavitron® W7 HP7 Pharma, CAS Registry Number 128446-35-5, which is a hydroxypropyl-beta-cyclodextrin having seven glucose units and a molecular substitution per anhydro glucose unit of 0.86-1.14 and Cavitron® W7 HP5 Pharma, which is a hydroxypropyl-beta-cyclodextrin having seven glucose units and a molecular substitution per anhydro glucose unit of 0.59-0.73.

Sulfoalkyl Ether Cyclodextrin Derivatives

Sulfoalkyl ether cyclodextrins useful herein include sulfoalkyl ether cyclodextrin derivatives further described in U.S. Pat. No. 5,874,418, to Stella et al., issued Feb. 23, 1999; U.S. Pat. No. 5,376,645, to Stella et al., issued Dec. 27, 1994, along with its certificate of correction of May 19, 2008; and U.S. Pat. No. 5,134,127, to Stella et al., issued Jul. 28, 1992, which are incorporated by reference herein in their entirety. These patents describe the sulfoalkyl ether cyclodextrins as follows:

This invention also provides cyclodextrin derivatives suitable for pharmaceutical use. These derivatives are suitable for use as clathrating agents with drugs to provide clathrate complexes which are useful in parenteral and other pharmaceutical formulations. Procedures for making and isolating the cyclodextrin derivatives are also provided.

The sulfoalkyl ether cyclodextrin derivatives of the present invention are functionalized with $(C_{2-6}$ alkylene)-$SO_3^-$ groups, and are thus charged species. The fact that these compounds have been discovered to possess a very low level of toxicity is surprising in light of the prior art's belief that cyclodextrin derivatives must retain electroneutrality to sustain lack of toxicity (cf. Pitha, "Amorphous Water-Soluble" "Third International Symposium on Recent Advances in Drug Delivery Systems, Salt Lake City, Utah, Feb. 23-27, 1987).

The high aqueous solubility of the cyclodextrin derivatives of the present invention, and their resulting lowered nephrotoxicity, is further surprising in light of U.S. Pat. No. 4,727,064's disclosure that to maintain a high level of solubility for cyclodextrin derivatives, a mixture of derivatives should be used.

The aqueous solubility exhibited by the present sulfoalkyl cyclodextrin derivatives appears to be obtained through solvation of the sulfonic acid moieties. Thus heterogeneous mixture of the present cyclodextrin derivatives is not a requirement for the observed enhanced solvation to occur. Although a mixture of sulfoalkyl ether derivatives can be used in accordance with the present invention, such a mixture is not required for enhanced solubility.

In an embodiment, the sulfoalkyl ether cyclodextrin derivatives of this invention have structures represented by formula (1) shown immediately below:

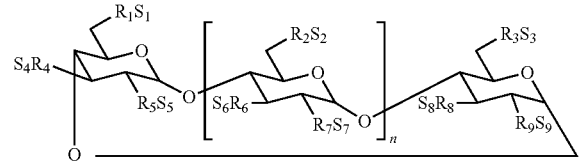

Formula 1 wherein: n is 4, 5 or 6;

$R_1, R_2, R_3, R_4, R_5, R_6, R_7, R_8$ and $R_9$ are each independently, $O^-$ or a $O-(C_{2-6}$ alkylene)-$SO_3^-$ group, wherein at least one of $R^1$ and $R^2$ is independently a $O-(C_{2-6}$ alkylene)-$SO_3^-$ group, for example a $O-(CH_2)_m-SO_3^-$ group, wherein m is 2 to 6, for example 2 to 4, (e.g. $OCH_2CH_2CH_2SO_3^-$ or $OCH_2CH_2CH_2CH_2SO_3^-$); and $S_1, S_2, S_3, S_4, S_5, S_6, S_7, S_8$ and $S_9$ are each, independently, a pharmaceutically acceptable cation which includes, for example, $H^+$, alkali metals (e.g. $Li^+$, $Na^+$, $K^+$), alkaline earth metals (e.g., $Ca^{+2}$, $Mg^{+2}$), ammonium ions and amines cations such as the cations $C_{1-6}$ alkylamines, piperidine, pyrazine, $C_{1-6}$ alkanolamine and $C_{4-8}$ cycloalkanolamine.

In another embodiment (2):

$R_1$ is a $O-(C_{2-6}$ alkylene)-$SO_3^-$ group, for example a $O-(CH_2)_m-SO_3^-$ group, (e.g. $OCH_2CH_2CH_2SO_3^-$ or $OCH_2CH_2CH_2CH_2SO_3^-$);

$R^2$ to $R^9$ are $O^-$; and $S_1$ to $S_9$ are as defined for formula 1, supra.

In another embodiment (3):

$R^1, R^2$ and $R^3$ are each, independently, a $O-(C_{2-6}$ alkylene)-$SO_3^-$ group, for example a $O-(CH_2)_mSO_3^-$ group, (e.g. $OCH_2CH_2CH_2SO_3$ or $OCH_2CH_2CH_2CH_2SO_3^-$);

$R^4$ to $R^9$ are $O^-$; and $S_1$ to $S_9$ are as defined for formula 1, supra.

In another embodiment (4):

$R^1$ to $R^3$ are as defined in embodiments (2) or (3); supra;

at least one of $R^4$, $R^6$ and $R^8$ is a O—$C_{2-6}$-alkylene-$SO_3^-$ group, for example a O—$(CH_2)_m SO_3^-$ group (e.g. $OCH_2CH_2CH_2SO_3$ or $OCH_2CH_2CH_2CH_2SO_3^-$).

$R_5$, $R_7$ and $R^9$ are O$^-$; and $S_1$ to $S_9$ are as defined for formula 1, supra.

In another embodiment (6):

$R_1$, $R_2$, $R_3$, $R_4$, $R_6$ and $R_8$ are each, independently, a O—($C_{2-6}$-alkylene)-$SO_3^-$ group, for example a O—$(CH_2)$—$_m SO_3^-$ group (e.g. $OCH_2CH_2CH_2SO_3$ or $OCH_2CH_2CH_2CH_2SO_3^-$);

$R^5$, $R^7$ and $R^9$ are O$^-$; and $S_1$ to $S_9$ are as defined for formula 1, supra.

The terms "alkylene" and "alkyl" in this text (e.g., in the O—($C_{2-6}$-alkylene)$SO_3^-$ group or in the alkylamines) include both linear and branched, saturated and unsaturated (i.e., containing one double bond) divalent alkylene groups and monovalent alkyl groups, respectively. The term "alkanol" in this text likewise includes both linear and branched, saturated and unsaturated alkyl components of the alkanol groups, in which the hydroxyl groups may be situated at any position on the alkyl moiety. The term "cycloalkanol" includes unsubstituted or substituted (e.g., by methyl or ethyl) cyclic alcohols.

In one embodiment, the present invention provides compositions containing a mixture of cyclodextrin derivatives having the structure set out in formula (1), where the composition overall contains on the average at least 1 and up to 3n+6 alkylsulfonic acid moieties per cyclodextrin molecule. The present invention also provides compositions containing essentially only one single type of cyclodextrin derivative.

In one embodiment, the present cyclodextrin derivatives are either substituted at least at one of the primary hydroxyl groups (i.e., at least one of $R_1$ to $R_3$ is a substituent), or they are substituted at both the primary hydroxyl group and at the 3-position hydroxyl group (i.e., both at least one of $R_1$ to $R_3$ and at least one of $R_4$, $R_6$ and $R_8$ are a substituent). In another embodiment, substitution at the 2-position hydroxyl group, while theoretically possible, does not appear to be substantial in the products of the invention. The cyclodextrin derivatives of the present invention are obtained (as discussed below) as purified compositions, for example as compositions containing at least 95 wt. % of cyclodextrin derivative(s) with the substitution occurring at least on the primary hydroxyl group of the cyclodextrin molecule (i.e. $R_1$, $R_2$ or $R_3$ of formula (1)), as determined by 300 MHz $^1$H NMR). In an embodiment, purified compositions containing at least 98 wt. % cyclodextrin derivative(s) can be obtained.

In one embodiment, this is to be contrasted with the U.S. Pat. No. 3,426,011 disclosure which reports obtaining only reaction products of the reaction of a cyclodextrin with a sulfone reactant. The reaction products in the '011 patent contain considerable quantities of unsubstituted cyclodextrin starting material.

In one embodiment of compositions of the invention, unreacted cyclodextrin has been substantially removed, with the remaining impurities (i.e., ≤5 wt. % of composition) being inconsequential to the performance of the cyclodextrin derivative-containing composition.

It should be noted that the variables used to describe the cyclodextrins are intended to be separate from the variables used to define the quinolone carboxylic acid derivatives.

The more highly substituted alkyl sulfonic acid cyclodextrin derivatives of the present invention have been discovered to possess, in addition to notably enhanced solubility characteristics and low toxicity, the advantageous property of causing less membrane disruption. In red blood cell hemolysis studies, the more highly substituted cyclodextrin derivatives demonstrated negligible membrane disruption. The mono-substituted cyclodextrin derivatives caused about the same amount of membrane disruption as the hydroxypropyl derivative.

In one embodiment, improved characteristics are achieved by purified compositions of the invention, containing <5%, for example less than 2%, of unreacted beta-cyclodextrin, for example for compositions to be administered to a patient by parenteral administration. In one embodiment, compositions containing somewhat higher amounts of unreacted beta-cyclodextrin, are useful for oral administration.

The allowance for residual beta-cyclodextrin can be broader for a sulfoalkylether cyclodextrin preparation when used in an oral formulation. The oral absorption of beta-cyclodextrin can sometimes be limited (if it occurs at all) and the elimination of beta-cyclodextrin in the feces would preclude any nephrotoxicity. However, the level of beta-cyclodextrin which might be tolerated in an oral formulation would still be dependent upon other characteristics of the material particularly on its intrinsic aqueous solubility.

In one embodiment, the sulfoalkylether cyclodextrins of the present invention may be used for oral formulations, even if unreacted beta-cyclodextrin is contained in an amount of up to about 50%. In one embodiment, the amount is limited to less than 40%. In one embodiment, the amount is limited to less than about 25%.

Preparation of the Cyclodextrin (CD) Derivatives:

The cyclodextrin derivatives described may be generally prepared by dissolving the cyclodextrin in aqueous base at an appropriate temperature, e.g., 70 degrees to 80 degrees C., at the highest concentration possible. For example, to prepare the cyclodextrin derivatives of an embodiment herein, an amount of an appropriate alkyl sulfone, corresponding to the number of moles of primary CD hydroxyl group present, is added with vigorous stirring to ensure maximal contact of the heterogeneous phase.

To prepare the cyclodextrin derivatives of an embodiment herein, a molar amount of the alkyl sulfone, corresponding to the number of moles of CD used, is used. As would be readily determinable by one of skill in this art, to prepare cyclodextrin derivatives of an embodiment herein, an amount of alkyl sulfone between that stated above is used. Other cyclodextrin derivatives provided by the present invention are prepared Mutatis Mutandis.

The mixtures are allowed to react until one phase results which is indicative of depletion of the alkyl sulfone. The reaction mixture is diluted with an equal volume of water and neutralized with an acid such as hydrochloric acid. The solution is then dialyzed to remove impurities followed by concentration of the solution by ultrafiltration.

The concentrated solution is then subjected to ion-exchange chromatography to remove unreacted cyclodextrin, and then freeze-dried to yield the desired product.

The CD used in this invention may be any CD obtained by known methods, e.g., by the action of cyclodextrin-glucanotransferase (CGTase, E.C., 2.4.1.19.) upon starch. Thus CD herein means alpha-CD in which six glucose units are linked together through alpha-1,4 bond, beta-CD in which seven glucose units are linked together, or gamma-CD in which eight glucose units are linked together, or a mixture thereof. In one embodiment, beta-CD is useful for production of partially derivatized products of broad utility.

As noted herein and depending on the cyclodextrin derivative sought, the amount of alkyl sulfone used as the derivatizing agent should be not more than about one molar equivalent, based on the number of primary hydroxyl groups present in the CD, although the optimum amount may be somewhat dependent on the reactant concentration. Lithium hydroxide, sodium hydroxide and potassium hydroxide may be used as the accelerator. In one embodiment, sodium hydroxide is useful because of its low cost. Its amount must be more than about 30 molar equivalents, and should preferably be in the range of 80 to 200 molar equivalents, with the reactant concentration being set at a level higher than 10% (wt/wt), preferably in the range of 40 to 60% (wt/wt). Any solvent which is substantially inert to the partial alkylation may be used as reaction medium. Typical examples are water, DMF, DMSO, and mixtures thereof. In one embodiment, the use of water alone eases after-treatment. The type and concentration of alkylsulfone and alkali are not critical to the reaction. However, the reaction is normally carried out with stirring at 10° to 80° C. for one hour, or at 20° to 50° C. for 5 to 20 hours.

Techniques commonly used in this field may be employed to isolate and purify the objective compounds from reaction mixtures. These include extraction with organic solvents, dialysis, adsorption chromatography with activated charcoal, silica gel, alumina and other adsorbents, chromatography using, as carrier, crosslinked dextrin, styrene/divinylbenzene copolymers and other cross-linked polymers, and combinations thereof.

Sulfoalkyl ether cyclodextrin derivatives useful herein include sulfobutyl ether cyclodextrins, including sulfobutyl ether beta-cyclodextrins.

An example of a sulfoalkyl ether cyclodextrin derivative useful herein includes Captisol, CAS Registry Number 194615-04-8.

The cyclodextrin comprises from about 1% to about 50% by weight of the composition. In further embodiments, the cyclodlextrin comprises from about 5% to about 40% by weight of the composition. In yet further embodiments, the cyclodextin comprises from about 10% to about 30% by weight of the composition. In yet further embodiments, the cyclodextrin comprises from about 15% to about 25% by weight of the composition.

c. Water

In one embodiment, the compositions of the present invention comprise from about 0.1% to about 99.9% water, in further embodiments from about 1% to about 99% water, in yet further embodiments from about 5% to about 95% water, and in yet further embodiments from about 10% to about 90% water. In defining a composition, the amount of water can be designated as "q.s." or "Q.S.", which means as much as suffices, to provide a final composition or volume of 100%.

d. Sugars and Sugar Alcohols

The compositions of the present invention, when further made into a lyophile, can further comprise a sugar, a sugar alcohol, or mixtures thereof. Without being limited by theory, these sugars and sugar alcohols are believed to aid in the formation of the lyophile during the lyophilization process. Typically, the lyophile is made by drying the composition under appropriate conditions, such as, for example, by freeze drying. Nonlimiting examples of sugars include mannose, sucrose, dextrose, sorbitol, mannitol, and mixtures thereof. Nonlimiting examples of sugar alcohols useful herein include mannitol and xylitol and mixtures thereof.

In one embodiment, the compositions comprise from about 0.1% to about 50% of a sugar or sugar alcohol.

e. Polyhydroxy Amine Compound

In one embodiment, the compositions of the present invention comprise a polyhydroxy amine compound. The polyhydroxy amine compound is separate from and does not encompass the polyhydroxy compound of the compositions of the present invention. The polyhydroxy amine compound is generally a $C_3$-$C_8$ straight, branched, or cyclic compound having 2 or more hydroxy substituents, and at least one amine (either substituted or unsubstituted) substituent.

In further embodiments the polyhydoxy amine compound is meglumine. Meglumine corresponds to CAS Registry Number 6284-40-8 and is also known as meglumine, USP; 1-Deoxy-1-(methylamino)-D-glucitol; N-Methyl-D-glucamine; Glucitol, 1-deoxy-1-(methylamino)-, D-(8Cl); Sorbitol, 1-methyl-1-methylamino-(6Cl); 1-Deoxy-1-(methylamino)-D-glucitol; 1-Deoxy-1-methylaminosorbitol; D-(−)-N-Methylglucamine; Meglumin; Methylglucamin; Methylglucamine; N-Methyl-D-(−)-glucamine; N-Methyl-D-glucamine; N-Methylglucamine; N-Methylsorbitylamine; NSC 52907; NSC 7391. It also has the CA Index Name D-Glucitol, 1-deoxy-1-(methylamino)-(9Cl). A chemical formula for meglumine is as follows:

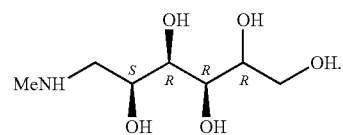

In one embodiment, the polyhydroxy amine compound comprises from about 0.1% to about 50% by weight of the composition. In further embodiments, the polyhydroxy amine compound comprises from about 0.25% to about 20% by weight of the composition. In yet further embodiments, the polyhydroxy amine compound comprises from about 0.5% to about 10% by weight of the composition. In yet further embodiments, the polyhydroxy amine compound comprises from about 1% to about 5% by weight of the composition.

f. Chelating Agents

The compositions of the present invention can further comprise a chelating agent. The chelating agent is defined herein as excluding the cyclodextin, the polyhydroxy amine compound, or any of the other components described herein, even though the cyclodextrin, the polyhydroxy amine compound, or other components described herein can also have chelating properties. An example of a chelating agent useful herein is EDTA, also known as ethylenediaminetetraacetic acid, or a salt thereof. Useful salts include, for example, a sodium salt, a potassium salt, a calcium salt, a magnesium salt, and mixtures of these salts. An example of a mixture of salts or a mixed salt is the monosodium monocalcium salt of EDTA. It is found that the disodium salt of EDTA, also known as disodium EDTA, is useful herein. For convenience, the disodium EDTA can first be separately prepared as an aqueous solution for use in formulating the compositions of the present invention.

In one embodiment, the disodium EDTA comprises from about 0.0010% to about 0.10% by weight of the composition. In further embodiments, the disodium EDTA comprises from about 0.0050% to about 0.050% by weight of the composition. In yet further embodiments, the disodium EDTA comprises from about 0.010% to about 0.020% by weight of the composition. In other embodiments the disodium EDTA comprises about 0.010% of the composition, or about 0.011% of the composition, or about 0.012% of the composition, or about 0.013% of the composition, or about 0.014% of the composition, or about 0.015% of the composition, or about 0.016% of the composition, or about 0.017% of the composition, or about 0.018% of the composition, or about 0.019% of the composition, or about 0.020% of the composition. These weight percentages of the disodium EDTA described herein are on the basis of the etheylenediaminetetracetic acid.

g. pH Modifiers and pH of the Compositions

The compositions of the present invention can further comprise various materials for modifying or adjusting the pH of the composition. Such materials include acids, bases, buffer systems, etc. Nonlimiting examples of such pH modifiers include, for example, hydrochloric acid and sodium hydroxide. Examples of other useful materials include triethanolamine, sodium carbonate, and lysine. Furthermore, the polyhydroxy amine compound, such as described above, can be used as a pH modifier. More specifically, the polyhydroxy amine compound, meglumine, can be used as a pH modifier.

The compositions of the present invention should have a pH so that the composition is suitable for administration to a patient or subject. The compositions have a pH from about pH 7 to about pH 11. In further embodiments, the compositions have a pH from about pH 8 to about pH 10. In further embodiments, the compositions have a pH from about pH 8.5 to about pH 9.5. In further embodiments, the compositions have a pH from about pH 8.8 to about pH 9.2. In further embodiments, the compositions have a pH of about 9.0.

h. Additional Components

The compositions of the present invention can further comprise one or more additional components selected from a wide variety of excipients known in the pharmaceutical formulation art. According to the desired properties of the tablet or capsule, any number of ingredients can be selected, alone or in combination, based upon their known uses in preparing the compositions of the present invention. Such ingredients include, but are not limited to solvents (e.g. ethanol); colorants; waxes, gelatin; preservatives (e.g., methyl paraben, sodium benzoate, and potassium benzoate); antioxidants [e.g., butylated hydroxyanisole ("BHA"), butylated hydroxytoluene ("BHT"), and vitamin E and vitamin E esters such as tocopherol acetate]; surfactants; UV-absorbers, etc.

In one embodiment, the compositions of the present invention comprise a carrier. The carrier can be a dextrose solution or saline, at a pharmaceutically acceptable concentration. The composition comprising a carrier can be administered to a patient via an i.v. bag.

3. Processing

The compositions of the present invention are made using convention equipment and mixing techniques.

Lyophilization, also known as freeze-drying is a dehydration process to remove the liquid, typically water and other relatively volatile solvents, from a material. Freeze drying works by freezing the material and then reducing the surrounding pressure and, as appropriate, adding enough heat to allow the frozen mobile water and other solvents in the material to sublime directly from the solid phase to gas.

4. Packaging

The compositions of the present invention can be packaged in standard, commercially available containers such as vials for liquid or lyophile storage. Generally, the vial is glass. The glass can be colorless or colored, clear or amber. Various types of closure systems can be used such as screw vials (closed with screw cap), lip vials (closed with a stopper), or crimp vials (closed with a rubber stopper and a metal cap).

Additionally, the compositions of the present invention, including a reconstituted lyophile, can be further diluted into an intravenous delivery bag or bottle.

The invention encompasses kits that can simplify the administration of a quinolone carboxylic acid derivative or a composition comprising it to a subject. In one embodiment, a kit of the invention comprises a unit dosage form of a quinolone carboxylic acid derivative. In one embodiment the unit dosage form is a container, which can be sterile, containing an effective amount of a quinolone carboxylic acid derivative and a physiologically acceptable carrier or vehicle. Physiologically acceptable carriers include saline and dextrose solutions at pharmaceutically acceptable concentrations. Such compositions can be contained in an i.v. drip bag. The kit can further comprise a label or printed instructions instructing the use of the quinolone carboxylic acid derivative to treat, prevent, or reduce the risk of an infection. Kits of the invention can further comprise a device that is useful for administering the unit dosage forms. Examples of such a device include, but are not limited to, a bottle, a vial, a syringe and a drip bag. Other examples of devices include, but are not limited to, a patch, an inhaler, and an enema bag. In one embodiment, the device that is useful for administering the unit dosage forms is the container.

5. Doses and Methods of Treating, Preventing, or Reducing the Risk of Infections The compositions of the present invention are useful for treating, preventing or reducing the risk of infection due to, e.g., a skin infection, nosocomial pneumonia, post-viral pneumonia, an abdominal infection, a urinary tract infection, bacteremia, septicemia, endocarditis, an atrio-ventricular shunt infection, a vascular access infection, meningitis, infection due to surgical or invasive medical procedures, a peritoneal infection, a bone infection, a joint infection, a methicillin-resistant *Staphylococcus aureus* infection, a vancomycin-resistant Enterococci infection, a linezolid-resistant organism infection, tuberculosis, a quinolone resistant Gram-positive infection, a ciprofloxacin resistant methicillin resistant (MRSA) infection, bronchitis, a complicated skin and skin structure infection (cSSSI), an uncomplicated skin and skin structure infection (uSSSI), a community respiratory-tract infection, and a multi drug resistant (MDR) Gram-negative infection.

The dose of active compound and mode of administration, e.g., injection, intravenous drip, etc. will depend upon the intended patient or subject and the targeted microorganism, e.g., the target bacterial organism. Dosing strategies are disclosed in L. S. Goodman, et al., *The Pharmacological Basis of Therapeutics*, 201-26 (5th ed. 1975), the entire contents of which is herein incorporated in its entirety.

Compositions can be formulated in dosage unit form for ease of administration and uniformity of dosage. Dosage unit form refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the therapeutic effect to be achieved, and the limitations inherent in the art of compounding such an active compound for the treatment of individuals. Furthermore, administration can be by periodic injections of a bolus, or can be made more continuous by intravenous, intramuscular or intraperitoneal administration from an external reservoir (e.g., an intravenous bag).

Where the active compound is to be used as part of a transplant procedure, it can be provided to the living tissue or organ to be transplanted prior to removal of tissue or organ from the donor. The compound can be provided to the donor host. Alternatively or, in addition, once removed from the donor, the organ or living tissue can be placed in a preservation solution containing the active compound. In all cases, the active compound can be administered directly to the desired tissue, as by injection to the tissue, or it can be provided systemically, by parenteral administration, using any of the methods and formulations described herein and/or known in the art. Where the drug comprises part of a tissue or organ preservation solution, any commercially available preservation solution can be used to advantage. For example, useful solutions known in the art include Collins solution, Wisconsin solution, Belzer solution, Eurocollins solution and lactated Ringer's solution.

In conjunction with the methods of the present invention, pharmacogenomics (i.e., the study of the relationship between an individual's genotype and that individual's response to a foreign compound or drug) can be considered. Differences in metabolism of therapeutics can lead to severe toxicity or therapeutic failure by altering the relation between dose and blood concentration of the pharmacologically active drug. Thus, a physician or clinician can consider applying knowledge obtained in relevant pharmacogenomics studies in determining whether to administer a drug as well as tailoring the dosage and/or therapeutic regimen of treatment with the drug.

Generally, an effective amount of dosage of active compound will be in the range of from about 0.1 to about 100 mg/kg of body weight/day. In one embodiment, the amount will be from about 1.0 to about 50 mg/kg of body weight/day. The amount administered will also likely depend on such variables as the overall health status of the patient, the relative biological efficacy of the compound delivered, the formulation of the drug, the presence and types of excipients in the formulation, the route of administration, and the infection to be treated, prevented, or reducing the risk of. Also, it is to be understood that the initial dosage administered can be increased beyond the above upper level in order to rapidly achieve the desired blood-level or tissue level, or the initial dosage can be smaller than the optimum.

Nonlimiting doses of active compound comprise from about 0.1 to about 1500 mg per dose. Nonlimiting examples of doses, which can be formulated as a unit dose for convenient administration to a patient include: about 25 mg, about 50 mg, about 75 mg, about 100 mg, about 125 mg, about 150 mg, about 175 mg, about 200 mg, about 225 mg, about 250 mg, about 275 mg, about 300 mg, about 325, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050, mg, about 1075 mg, about 1100 mg, about 1125 mg, about 1150 mg, about 1175 mg, about 1200 mg, about 1225 mg, about 1250 mg, about 1275 mg, about 1300 mg, about 1325 mg, about 1350 mg, about 1375 mg, about 1400 mg, about 1425 mg, about 1450 mg, about 1475 mg, and about 1500 mg. The foregoing doses are useful for administering the compounds of the present invention according to the methods of the present invention. The foregoing doses are particularly useful for administering the quinolone carboxylic acid derivatives of the present invention, particularly the compound known by the name delafloxacin and pharmaceutically acceptable salts, esters and prodrugs thereof.

As is understood by one of ordinary skill in the art, generally, when dosages are described for a pharmaceutical active, the dosage is given on the basis of the parent or active moiety. Therefore, if a salt, hydrate, or another form of the parent or active moiety is used, a corresponding adjustment in the weight of the compound is made, although the dose is still referred to on the basis of the parent or active moiety delivered. As a nonlimiting example, if the parent or active moiety of interest is a monocarboxylic acid having a molecular weight of 250, and if the monosodium salt of the acid is desired to be delivered to be delivered at the same dosage, then an adjustment is made recognizing that the monosodium salt would have a molecular weight of approximately 272 (i.e. minus 1H or 1.008 atomic mass units and plus 1 Na or 22.99 atomic mass units). Therefore, a 250 mg dosage of the parent or active compound would correspond to about 272 mg of the monosodium salt, which would also deliver 250 mg of the parent or active compound. Said another way, about 272 mg of the monosodium salt would be equivalent to a 250 mg dosage of the parent or active compound.

In one embodiment, compositions of the invention is useful in the manufacture of a medicament for treating, preventing or reducing the risk of infection in a patient in need thereof. In another embodiment, delafloxacin, or a pharmaceutically acceptable salt or ester thereof, is useful in the manufacture of a medicament for treating, preventing or reducing the risk of infection in a patient in need thereof. Such infections can be due to, e.g., a skin infection, nosocomial pneumonia, post-viral pneumonia, an abdominal infection, a urinary tract infection, bacteremia, septicemia, endocarditis, an atrio-ventricular shunt infection, a vascular access infection, meningitis, infection due to surgical or invasive medical procedures, a peritoneal infection, a bone infection, a joint infection, a methicillin-resistant *Staphylococcus aureus* infection, a vancomycin-resistant Enterococci infection, a linezolid-resistant organism infection, tuberculosis, a quinolone resistant Gram-positive infection, a ciprofloxacin resistant methicillin resistant (MRSA) infection, bronchitis, a complicated skin and skin structure infection (cSSSI), an uncomplicated skin and skin structure infection (uSSSI), a community respiratory-tract infection, and a multi drug resistant (MDR) Gram-negative infection.

Using delafloxacin as a nonlimiting example, an example of a composition useful in the methods of the present invention can contain about 300 mg of delafloxacin, or a pharmaceutically acceptable salt or ester thereof.

6. EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Ingredients are identified by chemical, USP, or CTFA name.

The following formulations are prepared using mixing techniques and equipment familiar to one of ordinary skill in the art.

These formulations are useful for intravenous administration, either infusion or bolus, such as injection, to a patient for treating, preventing, or reducing the risk of a microbial infection, e.g., a skin infection, including uncomplicated skin infections, skin and soft tissue infections, complicated skin infections, pneumonia, including e.g., community acquired pneumonia, nosocomial (hospital acquired) pneumonia, hospital acquired community pneumonia, post-viral pneumonia, an abdominal infection, a urinary tract infection, bacteremia, septicemia, endocarditis, an atrio-ventricular shunt infection, a vascular access infection, meningitis, infection due to surgical or invasive medical procedures, a peritoneal infection, a bone infection, a joint infection, a methicillin-resistant *Staphylococcus aureus* infection, a vancomycin-resistant Enterococci infection, a linezolid-resistant organism infection, and tuberculosis. More specifically, this formulation is useful for reducing the risk of or preventing infection due to a surgical or invasive medical procedure to be performed upon the patient, and in such case, the formulation can be administered just prior to or up to about 1 hour prior to the surgical or invasive medical procedure.

Example 1

Composition of Delafloxacin-Meglumine Formulation for Intravenous Administration

| Ingredient | Mg/mL | Batch size, mL % (weight/volume) | 1000 gram Batch Amt (g)/batch |
|---|---|---|---|
| Delafloxacin Meglumine (amount as free acid) | 20.000 | 2.00% | 20.000 |
| Meglumine (anhydrous, mw 195.21) | 4.88 | 0.49% | 4.880 |
| Captisol | 200 | 20.00% | 200 |
| Water for Injection | q.s. | q.s. | q.s. |
| 1N NaOH and/or HCl acid | q.s. | q.s. | q.s. |
| Density | 1.082 g/ml | | |
| Final pH | 9.0 (±0.1) | | |

API supplied as Meglumine salt of delafloxacin, 28.86 mg/mL Delafloxacin Meglumine salt=20 mg/mL as free base
Conversion factor between RX-3341 salt/free acid=1.4429
Volume for 150 mg dose, mL 8
Procedure:
1. Weigh Water for Injection approximately 70% of the total batch weight into a suitable container.
2. Add the required amount of captisol (beta-Cyclodextrin sulfobutyl ether sodium) to the solution and mix until dissolved.
3. Add the required amount of Meglumine to the solution and mix until dissolved.
4. Add the required amount of delafloxacin corrected for purity and salt content and mix until dissolved.
5. Test for pH. The target pH is 9.0 (0.1).
Adjust with Hydrochloric Acid (as a 1N solution) or Sodium Hydroxide (as a 1N solution) as needed.
6. q.s. to the final weight or volume with Water for Injection.
7. Sterile filter solution (two filters 0.22 um) and fill into vials.

Based on the above foregoing formulation table, the following mg of the indicated component is delivered in a given dosage.

| | 100 mg strength dosage | 300 mg strength dosage | 500 mg strength dosage |
|---|---|---|---|
| Delafloxacin | 100 mg | 300 mg | 500 mg |
| Meglumine | 24.4 mg | 73.2 mg | 122 mg |
| Captisol | 1000 mg | 3000 mg | 5000 mg |

The foregoing composition is useful for intravenous administration to a patient for treating, preventing, or reducing the risk of a microbial infection.

Example 2

Composition of Delafloxacin-Meglumine Formulation for Intravenous Administration

| Ingredient | Mg/ml | Batch size, mL % (weight/volume) | 1000 gram Batch Amt (g)/batch |
|---|---|---|---|
| Delafloxacin Meglumine (amount as free acid) | 25.000 | 2.50% | 25.000 |
| Meglumine (anhydrous, mw 195.21) | 4.88 | 0.49% | 4.880 |
| Captisol | 200 | 20.00% | 200 |
| Disodium EDTA, 0.1M Solution | 0.11* | 0.011% | 0.11 |
| Water for Injection | q.s. | q.s. | q.s. |
| 1N NaOH and/or HCl acid | q.s. | q.s. | q.s. |
| Density | 1.087 g/ml | | |
| Final pH | 9.0 (±0.1) | | |

API supplied as Meglumine salt of delafloxacin, 28.86 mg/mL Delafloxacin Meglumine salt=20 mg/mL as free base
The disodium EDTA concentration is expressed on a free acid basis.
Conversion factor between delafloxacin salt to free acid is 1.4429
Volume for 150 mg dose, mL 6
Procedure:
1. Weigh Water for Injection approximately 70% of the total batch weight into a suitable container.
2. Add the required amount of captisol (beta-Cyclodextrin sulfobutyl ether sodium) to the solution and mix until dissolved.
3. Add the required amount of Meglumine to the solution and mix until dissolved.

4. Add the EDTA solution and mix.
5. Add the required amount of delafloxacin corrected for purity and salt content and mix until dissolved.
6. Test for pH. The target pH is 9.0 (0.1).
   Adjust with Hydrochloric Acid (as a 1N solution) or Sodium Hydroxide (as a 1N solution) as needed.
7. q.s. to the final weight or volume with Water for Injection.
8. Sterile filter solution (two filters 0.22 um) and fill into vials.

*In further formulations, the amount of EDTA solution added is increased to 0.15 mg/mL.

The foregoing composition is useful for intravenous administration to a patient for treating, preventing, or reducing the risk of a microbial infection.

Based on the above foregoing formulation table, the following mg of the indicated component is delived in a given dosage.

|  | 100 mg strength dosage | 300 mg strength dosage | 500 mg strength dosage |
|---|---|---|---|
| Delafloxacin | 100 mg | 300 mg | 500 mg |
| Meglumine | 19.52 mg | 58.56 mg | 97.6 mg |
| Captisol | 800 mg | 2400 mg | 4000 mg |
| Disodium EDTA | 0.44 mg | 1.32 mg | 2.2 mg |

Example 3: Lyophilisates for Reconstitution for Intravenous Administration

Formulations can also be prepared as lyophilisates. For example, the formulations of Examples 1 and 2, above can also be prepared as lyophiles. This is accomplished by sterile filtering the solutions into lyophile vials, and then freeze drying the vials using conventional freeze drying techniques.

Such formulations are reconstituted with water or another appropriate aqueous based solution. These lyophilisates are a compact and convenient form to store the formulation.

Example 4. Solubility

The solubility of the quinolone carboxylic acid antimicrobial active in the compositions of the present invention is evaluated.

For room temperature equilibrium solubility measurements, an excess of the quinolone carboxylic acid antimicrobial compound to be evaluated is mixed with a test vehicle. The initial pH is recorded and then the pH is adjusted to the target pH for the study with either HCl or NaOH. Samples are placed at 25° C. in a rotating shaker at 200 rpm for 24 to 72 hours, with multiple timepoints generally taken for each sample to ensure that equilibrium has been reached. For each timepoint an aliquot is removed and centrifuged at 14K rpm for 10 minutes. The supernantant is decanted and the pH was measured. A sample was then diluted with methanol for HPLC analysis.

For 4° C. solubility measurements, a sample of the supernatant from the room temperature solubility study is placed at 4° C. Multiple timepoints are generally taken to ensure that equilibrium has been reached. For each timepoint an aliquot is removed and centrifuged at 14K rpm for 10 minutes while the sample is still cold. The supernantant is decanted and the pH is measured once the sample warms to room temperature. A sample is then diluted with methanol for HPLC analysis.

It is found that the compositions of the present invention provide better solubility, i.e. have enhanced solubility, for the quinolone carboxylic acid antimicrobial agent, compared to compositions outside of the present invention.

Example 5. Stability

The stability of the compositions of the present invention is evaluated.

Stability samples are placed on a stability test at −20, 4, 40, and 55° C., and at room temperature. The samples are placed in 20 mL serum crimp vials (Wheaton) with Gray Bromobutyl 39 Fluorinated Polymer stoppers (Wheaton). The pH, concentration, and stability profile are measured at 10 days, 1 month, 2 months, and 3 months. Samples at −20° C. are thawed prior to analysis by thawing at room temperature until no more ice is present and then placing in a 37° C. water bath for 10 minutes. Samples are then shaken or agitated briefly (approximately 15 seconds) to ensure all the solids are dissolved.

It is found that the compositions of the present invention provide compositions having enhanced stability, compared to compositions outside of the present invention.

Example 6. Venous Toleration

The venous toleration of the compositions of the present invention can be evaluated in vivo in a rat tail model. To study venous toleration, the composition of interest is infused using a peristaltic pump into a single vein in a rat tail. Compositions are infused on consecutive days, up to about five days. Each daily infusion is over a period of about one hour at the rate of 10 ml/kg/hr. The condition of the rattail is visually assessed using a grading scale. The venous tolerability of the composition is assessed from the condition of the rat tail and from the number of consecutive days the composition can be infused. In other words, a composition that can be successfully infused on four consecutive days has a better venous toleration than a composition that can only be successfully infused on two consecutive days. Appropriate control compositions can also be evaluated. It is found that the compositions of the present invention are better tolerated, i.e. have enhanced venous toleration, compared to compositions outside of the present invention.

For measuring the venous toleration, rats are placed under a heat lamp for warming. They are restrained throughout the infusion period by use of the Advance Infusion System (CellPoint Scientific). The rat is placed within a triangular 6 mil polyethylene bag (DecapiCone, Braintree Scientific). The bagged rodent is then held in place on the infusion table (15¾"×15¾") using 3 body restraint bands made of silicone tubing. An Abbocath-T (G720-A01, 4535-24, 24 G×¾", Abbott, Ireland) indwelling catheter is placed in either the right or left lateral tail vein, and secured in place at the site of insertion with surgical tape (3M, Hypoallergenic Micropure). Correct placement is confirmed by flashback of blood into catheter. A 16" IV extension set (Baxter, 2C5643) attached to a 5 ml syringe and pre-primed with dosing solution is attached to the indwelling catheter and secured in place by surgical tape. A 1 hr. slow infusion (10 ml/kg/hour) of compound is administered by Harvard Apparatus Infusion Pump. Following the infusion, the surgical tape is removed and the catheter is gently pulled from the site of insertion, while applying light pressure with gauze. The tails are cleaned of any residual blood by washing with warm water. The rats are then removed from the Decapi-Cone bag and returned to their cage.

INCORPORATION BY REFERENCE

The entire disclosure of each of the patent documents, including certificates of correction, patent application documents, scientific articles, governmental reports, websites, and other references referred to herein is incorporated by reference in its entirety for all purposes.

EQUIVALENTS

The invention can be embodied in other specific forms without departing from the spirit or essential characteristics thereof. The foregoing embodiments are therefore to be considered in all respects illustrative rather than limiting on the invention described herein.

What is claimed is:

1. An intravenous pharmaceutical composition comprising:
   (a) a quinolone carboxylic acid derivative or a pharmaceutically acceptable salt or ester thereof, wherein the quinolone carboxylic acid derivative corresponds to the following compound (A):

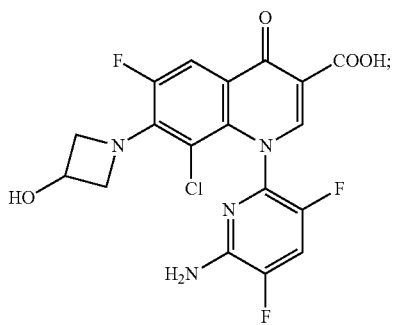 [SMILES: Nc1nc(-n2cc(C(=O)O)c(=O)c3cc(F)c(N4CC(O)C4)c(Cl)c32)c(F)cc1F]

(b) meglumine;
   (c) a SBE-7-β-CD; and
   (d) disodium EDTA.

2. The intravenous pharmaceutical composition according to claim 1, wherein the quinolone carboxylic acid derivative is a D-glucitol,1-deoxy-1-(methylamino)-, 1-(6-amino-3,5-difluoro-2-pyridinyl)-8-chloro-6-fluoro-1,4-dihydro-7-(3-hydroxy-1-azetidinyl)-4-oxo-3-quinolinecarboxylate (salt).

3. The intravenous pharmaceutical composition according to claim 2 wherein said quinolone carboxylic acid derivative is a crystalline D-glucitol, 1-deoxy-1-(methylamino)-, 1-(6-amino-3,5-difluoro-2-pyridinyl)-8-chloro-6-fluoro-1,4-dihydro-7-(3-hydroxy-1-azetidinyl)-4-oxo-3-quinolinecarboxylate (salt) characterized, when measured at about 25° C. with Cu-Ka radiation, by the powder diffraction pattern shown in FIG. 1.

4. The intravenous pharmaceutical composition according to claim 1, wherein the quinolone carboxylic acid derivative has a measurable improvement in solubility compared to the quinolone carboxylic acid derivative in water, and/or the composition has improved stability, and/or the composition provides a measurable enhancement in venous toleration.

5. The intravenous pharmaceutical composition according to claim 1 which is in the form of a lyophile.

6. The intravenous pharmaceutical composition according to claim 1, wherein the cyclodextrin comprises from 0.01% to 50% by weight of the composition.

7. The intravenous pharmaceutical composition according to claim 6, wherein the cyclodextrin comprises from 10% to 30% by weight of the composition.

8. The intravenous pharmaceutical composition according to claim 1, wherein the composition has a pH from 7 to 11.

9. The intravenous pharmaceutical composition according to claim 8, wherein the composition has a pH from 8 to 10.

10. The intravenous pharmaceutical composition according to claim 9, wherein the composition has a pH from 8.5 to 9.5.

11. The intravenous pharmaceutical composition according to claim 10, wherein the composition has a pH from 8.8 to 9.2.

12. The intravenous pharmaceutical composition according to claim 11, wherein the composition has a pH of 9.0.

13. An intravenous pharmaceutical composition comprising:
    (a) from 100 mg to 500 mg of delafloxacin,
    (b) from 15 mg to 125 mg meglumine,
    (c) from 500 mg to 5000 mg of a SBE-7-β-CD; and
    (d) from 0 mg to 4 mg disodium EDTA.

14. The intravenous pharmaceutical composition according to claim 13 comprising:
    (a) 100 mg of delafloxacin;
    (b) 19.52 mg of meglumine;
    (c) 800 mg of the SBE-7-β-CD; and
    (d) 0.44 mg of disodium EDTA.

15. The intravenous pharmaceutical composition according to claim 13 comprising:
    (a) 300 mg of delafloxacin;
    (b) 58.56 mg of meglumine;
    (c) 2400 mg of the SBE-7-β-CD; and
    (d) 1.32 mg of disodium EDTA.

16. The intravenous pharmaceutical composition according to claim 13 comprising:
    (a) 500 mg of delafloxacin;
    (b) 97.6 mg of meglumine;
    (c) 4000 mg of the SBE-7-β-CD; and
    (d) 2.2 mg of disodium EDTA.

17. The intravenous pharmaceutical composition according to claim 13 which is in the form of a lyophile.

18. The intravenous pharmaceutical composition according to claim 13, wherein the quinolone carboxylic acid derivative has a measurable improvement in solubility compared to the quinolone carboxylic acid derivative in water, and/or the composition has improved stability, and/or the composition provides a measurable enhancement in venous toleration.

19. The intravenous pharmaceutical composition according to claim 13, wherein the composition has a pH from 7 to 11.

20. An intravenous pharmaceutical composition comprising:
    (a) from 100 mg to 500 mg of delafloxacin meglumine,
    (b) from 15 mg to 125 mg meglumine,
    (c) from 500 mg to 5000 mg of the SBE-7-β-CD; and
    (d) from 0 mg to 4 mg disodium EDTA.

* * * * *